United States Patent
Aitken

(10) Patent No.: US 6,433,022 B1
(45) Date of Patent: Aug. 13, 2002

(54) SPERMICIDE

(75) Inventor: Robert John Aitken, Newcastle (AU)

(73) Assignee: Medical Research Council, London (GB)

( * ) Notice: Subject to any disclaimer, the term of this patent is extended or adjusted under 35 U.S.C. 154(b) by 0 days.

(21) Appl. No.: 09/381,011

(22) PCT Filed: Mar. 12, 1998

(86) PCT No.: PCT/GB98/00756

§ 371 (c)(1),
(2), (4) Date: Sep. 13, 1999

(87) PCT Pub. No.: WO98/40057

PCT Pub. Date: Sep. 17, 1998

(30) Foreign Application Priority Data

Mar. 12, 1997 (GB) ............................................. 9705110

(51) Int. Cl.[7] ......................... A61K 31/12; A61K 31/52; A61K 31/34
(52) U.S. Cl. ....................... 514/682; 514/681; 514/266; 514/461
(58) Field of Search ............................... 514/682, 266, 514/461, 681

(56) References Cited

FOREIGN PATENT DOCUMENTS

| WO | WO 94 02125 | 2/1994 |
| WO | WO 94 23742 | 10/1994 |
| WO | WO 96 29067 | 9/1996 |

OTHER PUBLICATIONS

Michiels et al., Eur. J. Biochem. (1988), 177(2), 435–441.*
R.J. Aitken, et al.: "Reactive Oxygen Species Generation By Human Spermatozoa", Molecular Reproduction and Development, vol. 47, No. 4, Aug. 1997, pp. 468–482, XP002071252, Wiley–Liss, Inc.
A. De Peyster, et al.: "Oxygen Radical Formation Induced By Gossypol In Rat Liver Microsomes And Human Sperm", Biochemical and Biophysical Research Communications, vol. 118, No. 2, 1984, pp. 573–579, XP002071253, Academic Press, Inc.
M. Rajasekaran, et al.: "Spermicidal Activity Of An Antifungal Saponin Obtained From The Tropical Herb Mollugo Pentaphylla", Contraception, vol. 47, No. 4, 1993, pp. 401–412, XP002071254, Butterworth–Heineman.
P. Kumar, et al.: "The Effect Of Some Of The Polyphenolic Compounds On Sperm Motility In Vitro: A Structure–Activity Relationship", Contraception, vol. 39, No. 5, 1989, pp. 531–539, XP002071255.

R.J. Aitken, et al.: "Use Of A Xanthine Oxidase Free Radical Generating System To Investigate The Cytotoxic Effects Of Reactive Oxygen Species On Human Spermatozoa", Journal of Reproduction and Fertility, vol. 97, No. 2, 1993, pp. 441–450, XP002071256, Journals of Reproduction and Fertility, Ltd.
K. Ollinger, et al.: "Effect of Hydroxy Substituent Position On 1,4–Naphthoquinone Toxicity to Rat Hepatocytes", The Journal of Biological Chemistry, vol. 266, No. 32, 1991, pp. 21496–21503, XP002071257, The American Society of Biochemistry and Molecular Biology, Inc.
R. Jones, et al.: "Peroxidative Breakdown Of Phospholipids In Human Spermatoza, Spermicidal Properties Of Fatty Acid Peroxides, And Protective Action Of Seminal Plasma", Fertility and Sterility, vol. 31, No. 5, 1979, pp. 531–537, XP002071258, The American Fertility Society, United States of America.
Y.Take, et al.: "Comparative Studies Of The Inhibitory Properties Of Antibiotics On Human Immunodeficiency Virus And Avian Myeloblastosis Virus Reverse Transcriptases And Cellular DNA Polymerases", the Journal of Antibiotics, vol. XLII, No. 1, 1989, pp. 107–115, XP002071259.
R.J. Aitken: "Free Radicals, Lipid Peroxidation And Sperm Function", Reproduction, Fertility and Development, vol. 7, No. 4, 1995, pp. 659–668, XP002071260.
Database WPI, Section Ch, Week 9347, Derwent Publications Ltd., London, Great Britain; Class B06, AN 93–369193, XP002071261 & BR 9 200 689 A (Vilaca Castro J), Aug. 1993.

* cited by examiner

Primary Examiner—Russell Travers
Assistant Examiner—S. Jiang
(74) Attorney, Agent, or Firm—Charles N. Quinn, Esq.

(57) ABSTRACT

There is provided a method of contraception, comprising exposing a spermicidally sufficient quantity of an agent to spermatozoa. The agent is a quinone represented by the following formula:

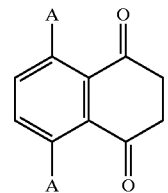

Figure 1A:
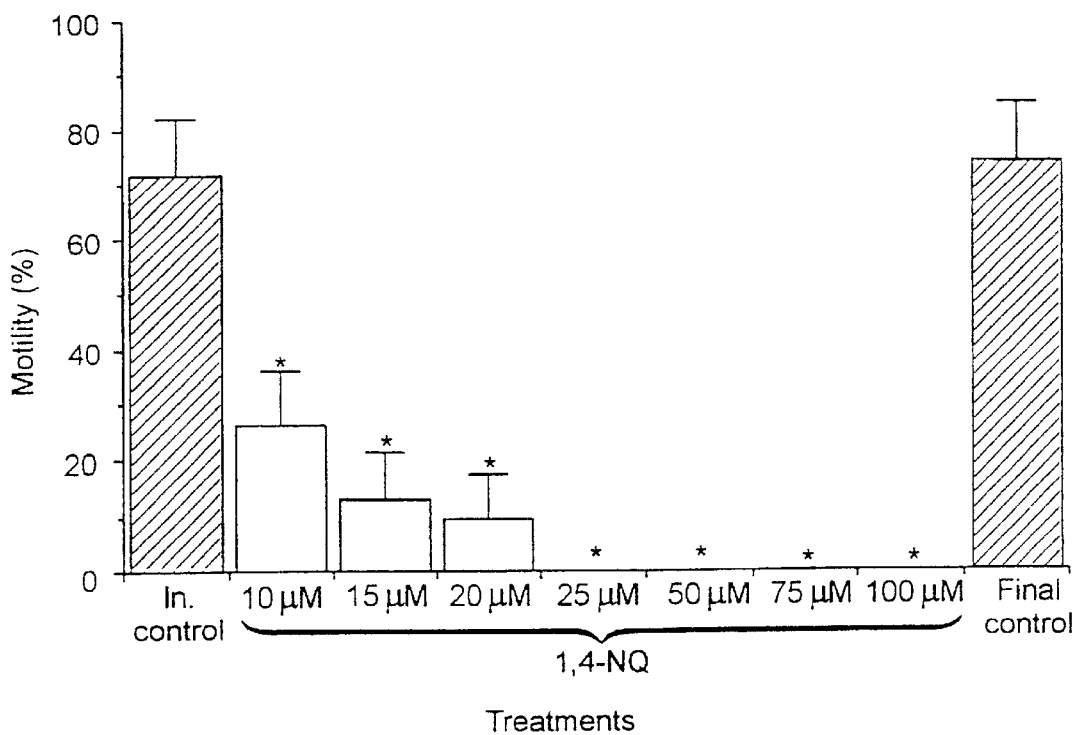

Each group A is H or an electron releasing moiety. The agent is capable of generating reactive oxygen species including free radicals, superoxide and hydrogen peroxide in the presence of spermatozoa.

2 Claims, 15 Drawing Sheets

SPERMICIDE

CROSS-REFERENCE TO RELATED APPLICATIONS

This patent application is a national phase application filed under 35 U.S.C. 371(c) based on and claiming the priority of PCT/GB98/00756, filed Mar. 12, 1998, which in turn claimed the priority of UK 97-051110.6 filed March 12, 1997, the priority of both of which are claimed under 35 U.S.C. 119, 120 and 365. International application PCT/GB98/00756 was published in English under PCT Article 21(2).

This invention relates to a spermicide.

Conventional spermicides have traditionally been active compositions not specifically activated by coitus. The best known spermicide is the detergent nonoxynol-9 (N-9), which is used to impregnate sponges which fit over the cervix, or is used to coat condoms etc. N-9 is believed to act by causing leakage of the intracellular contents, but does not easily diffuse through semen. There are also fears as to its effects on male foetuses, and that it may encourage genital ulcers when used frequently.

Human spermatozoa generate reactive oxygen species (ROS) which are involved in a number of key physiological events within sperm including hyperactivated sperm motility and the acrosome reaction, events intimately associated with oocyte sperm fusion. During spermiogenesis, spermatozoa undergo a peculiar morphological transformation in that most of their cytoplasm is discarded just prior to spermiation (release of sperm into the seminiferous tubules). Consequently they lose much of their intracellular defences against the effects of ROS and are thus left with a diminished amount of antioxidants such as, catalase (CAT), glutathione peroxidase and superoxide dismutase (SOD). Therefore, sperm have the difficult task of ensuring the balanced production of these biologically important modulators of cellular function.

Spermatozoa are uniquely susceptible to peroxidative damage initiated by excess production of reactive oxygen species (ROS). Moreover, ROS can initiate a lipid peroxidation cascade in the plasma membrane of the spermatozoa due to the high unsaturated fatty acid content of these cells. The double bonds found in the membrane weaken C—H bonds on the adjacent carbon atom, thus facilitating the hydrogen abstraction step of lipid peroxidation by ROS. This results in a loss of double bonds, and consequently, membrane fluidity. The direct impact of loss of membrane fluidity on the fusogenicity of the plasma membrane is demonstrated by the failure of peroxidised cells to exhibit normal rates of sperm-oocyte fusion. The activity of key membrane-bound enzymes, such as $Ca^{2+}$-$Mg^{2+}$-ATPases (Ohta et al, 1989) are also disrupted by the loss of membrane fluidity; consequently the spermatozoa lose their capacity to regulate the intracellular concentration of ions involved in the control of sperm movement. The biochemical mechanisms responsible for ROS generation in such cells are poorly understood.

According to the present invention there is provided a spermicidal agent which, upon contact with spermatozoa, is capable of generating reactive oxidizing species, including free radicals and hydrogen peroxide.

The generation of such oxidizing species is preferably in the form of a transient burst; this can overcome the limited endogenous protection mechanisms present in the spermatozoa and rapidly induce a loss of function of the sperm.

By "free radical" we mean any atom or group of atoms with an unpaired electron. Free radicals are generally capable of independent existence in that state.

The spermicidal activity is attributable to the capability of generating oxidizing species including free radicals. Suitable oxidants include any ROS such as superoxide ($O_2^-$) or hydrogen peroxide ($H_2O_2$).

The free radicals preferably kill sperm by disrupting the plasma membrane.

One advantage of the invention is that the spermicidal activity of the ROS may be deleterious to pathogenic microorganisms (eg fungi, bacteria and viruses), particularly enveloped viruses, since the ROS may disrupt any membranes present in the virions. Thus, the invention will be of utility to prevent or combat sexually transmitted diseases caused by microorganisms. Particular mention may be made of Chlamydia and HIV.

The invention also has the advantage that the vaginal tissues are not susceptible to damage by ROS such as hydrogen peroxide since the latter is continuously generated by the vaginal microflora, as a means of maintaining sterility.

Preferred examples of spermicidal ROS generators include quinones. Quinones are pharmacological agents with a wide range of clinical applications including use as antitumour agents for example adriamycin and dioxorubicin, antibiotics and antiparasitic drugs.

Multiple molecular mechanisms are involved in the cytotoxic actions of these compounds including the ability to redox cycle producing cytotoxic ROS (Kappus and Sies, 1981; Thor et al, 11982; Hoehsteim, 1983).

By harnessing endogenous sperm flavoprotein reductases such as NAD(P)H cytochrome P450 reductase and DT diaphorase, it is proposed that redox cycling quinones could potentially undergo a series of 1 and 2 electron reductions respectively. One electron reduction of the quinone produces a reactive semiquinone intermediate which redox cycles with $O_2$ producing superoxide anion radicals. The reaction of this superoxide anion with hydrogen peroxide, previously formed by the enzymatic or spontaneous dismutation of the superoxide anion radical, produces powerful oxidising hydroxy radicals. Indeed quinone-induced production of excessive amounts of ROS may overwhelm the inherent but limited protective mechanisms of the sperm resulting in the lipid peroxidation of polyunsaturated lipids present in the sperm membrane and eventual sperm death.

Whilst the invention is not limited to any particular compound, quinones of the following general formula are of special interest:

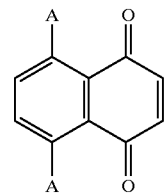

wherein each group A independently represents H or an electron releasing moiety. If present each or either of the electron relating moieties may operate by electron induction, in which case A will represent an alkyl group, aryl (especially phenyl)/or alkyl group. More preferably however each or either of the electron releasing moieties (if present) will be electron donating and suitable examples include —OH; —OR; —NH₂; —NHR; —N(R)₂; —SH; —SR (where each group R may independently be an alkyl group, especially a $C_{1-6}$ alkyl group, for example —CH₃;

—$CH_2CH_3$ etc). Where each group A represents H, the quinone is 1,4- napthoquinone. Upon exposure to sperm, this is transiently converted to a semiquinone with an additional $H^+$ ion. The semiquinone is an unstable molecule and decomposes back to 1,4-napthoquinone with a concomitant release of a single electron. The electron reduces $O_2$ to superoxide ($O_2^-$) which may be converted into hydrogen peroxide ($H_2O_2$) by superoxide dismutase (SOD). Mention may also be made of —OH substituted quinones on the first benzyl ring, for example, juglone.

Thus the present invention also provides a method of affecting the viability of spermatozoa, or their ability to fuse with an ovum, the method comprising producing a biologically effective amount of ROS. Generally the ROS will be generated within the female reproductive tract.

The present invention also provides the use of an agent capable of generating ROS (preferably upon contact with spermatozoa) as a spermicide.

The composition can be augmented by the provision of substances which inhibit enzymes or other agents capable of inhibiting the biologically active amount of ROS or $H_2O_2$. A good example of such substances are inhibitors of the enzyme glutathione peroxidase, such as mercaptosuccinate.

Although we do not wish to be bound by hypothesis, it is feasible that the cytotoxic action of ROS on sperm is due to the modification (eg oxidation or alkylation) of essential thiol groups or other cellular nucleophiles in (or on the surface of) the sperm.

The composition may be employed in a number of different ways, preferred methods being impregnation into sponges, as a coating onto barrier contraceptive devices and as pessaries.

Quinones are probably found in all respiring animal and plant cells. They occur as compounds of potential toxicological significance in foodstuffs and environmental pollutants (Thompson, 1971; Prior et al, 1982). They are also widely used as anticancer, antibacterial or antimalarial drugs as well as fungicides (O'Brien, 1991). Quinones such as adriamycin and dioxorubicin are anticancer agents and it is generally believed that they work by causing strand scission of DNA, insertion of the planar rings into DNA and the consequent inhibition of cellular RNA and DNA-dependent replication and transcription processes (Shinha and Sik, 1980; Lown et al, 1977). It is believed that quinone cytotoxicity is related to "oxidative stress" arising from the capacity of these compounds to redox cycle (Kappus and Sies, 1981; Thor et al, 1982; Hoehsteim, 1983).

Most biological electron flow is conducted to oxygen by a chain of carriers terminating in a cyanide-sensitive cytochrome oxidase which accomplishes the tetravalent reduction of dioxygen to water without the release of intermediates (Chance, 1952; Antonmi et al, 1970). Quinones can enter cells, accept electrons from one of the electron carriers, and give rise to an autoxidisable form could divert a portion of this electron flow to the production of $O_2^-$ and $H_2O_2$. 1,4 naphthoquinone is preferred. Lawsone, plumbagin, and especially juglone are other examples of useful quinones.

The ROS generated is preferably $O_2^-$ (superoxide) and hydrogen peroxide (which can be generated by dismutation of superoxide either spontaneously or under the influence of SOD).

Most semiquinones rapidly reduce dioxygen to form $O_2^-$ and thus regenerate the quinone. Therefore quinones can enter flavoprotein-catalysed redox cycles with dioxygen which results in the formation of significant amounts of $O_2^-$ and the oxidation of reduced pyridine nucleotides (Thor et al, 1982).

Dihydronicotinamide adenine dinucleotide phosphate (NADPH) is at least one source of electrons for the reduction of oxygen to give the superoxide anion i.e. administration of exogenous NADPH results in stimulated superoxide anion generation by human spermatozoa via the enzyme NADPH-oxidase-like enzyme present in sperm. The $O_2^-$ generated by the spermatozoa would then be expected to dismutate rapidly (using SOD) to give $H_2O_2$ (Aitken and Clarkson, 1987a, b; Alvarez et al, 1987; Lamuande and Gagnon, 1992) which is thought to be far more cytotoxic to the cell than $O_2^-$.

Due to the limited amount of cytoplasm present in spermatozoa, there is limited availability of NADPH and the normal fertile male produces extremely low levels of ROS (Aitken and Clarkson, 1987a, b; Aitken et al, 1989). However there is a heightened capacity for ROS generation in infertile men. Thus, the invention also provides the addition of an electron donor, such as NAD(P)H, to the composition either in addition to the substance, or as said substance, in order to enhance or provide its cytotoxic activity.

The cytotoxic activity of the substance may be effective against all forms of enveloped microorganisms, such as protozoa and bacteria.

The invention also provides for the addition of an electron donor, such as NAD(P)H, to the composition either in addition to the substance or as said substance, in order to enhance its spermicidal (cytotoxic) activity.

BRIEF DESCRIPTION OF THE DRAWING FIGURES

The present invention will now be described by way of non-limiting illustration, with reference to the following examples and figures.

FIG 1a. Dose response of 1,4-naphthoquinone on sperm motility.

Figure 1B:
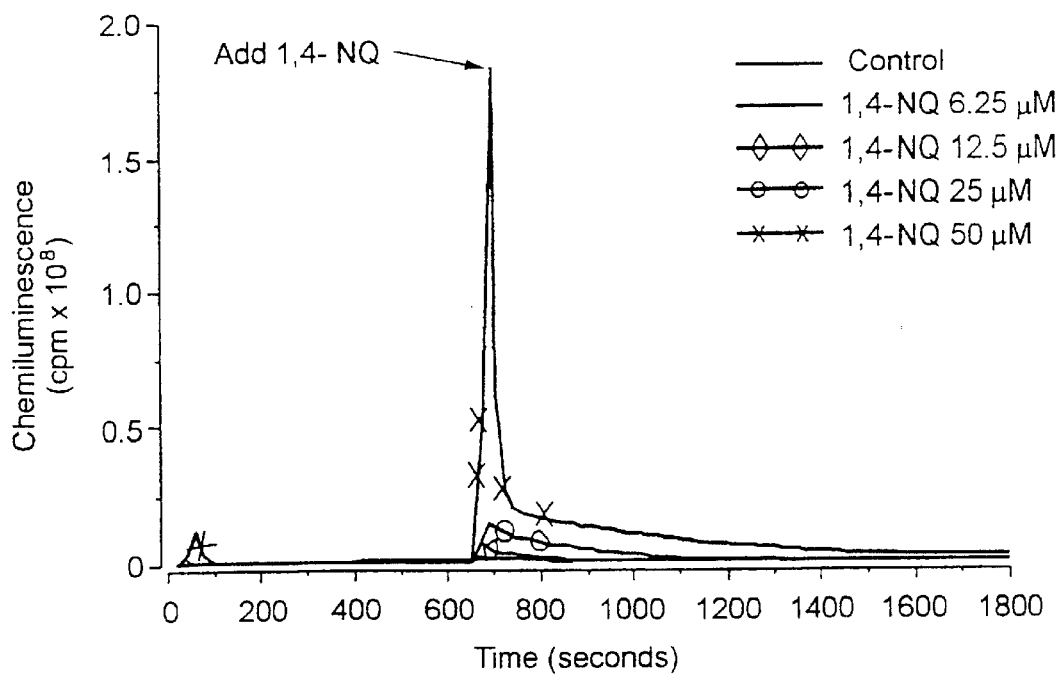

FIG. 1b. Chemiluminescence of 1,4-naphthoquinone induced hydrogen peroxide production in sperm.

Figure 1C:
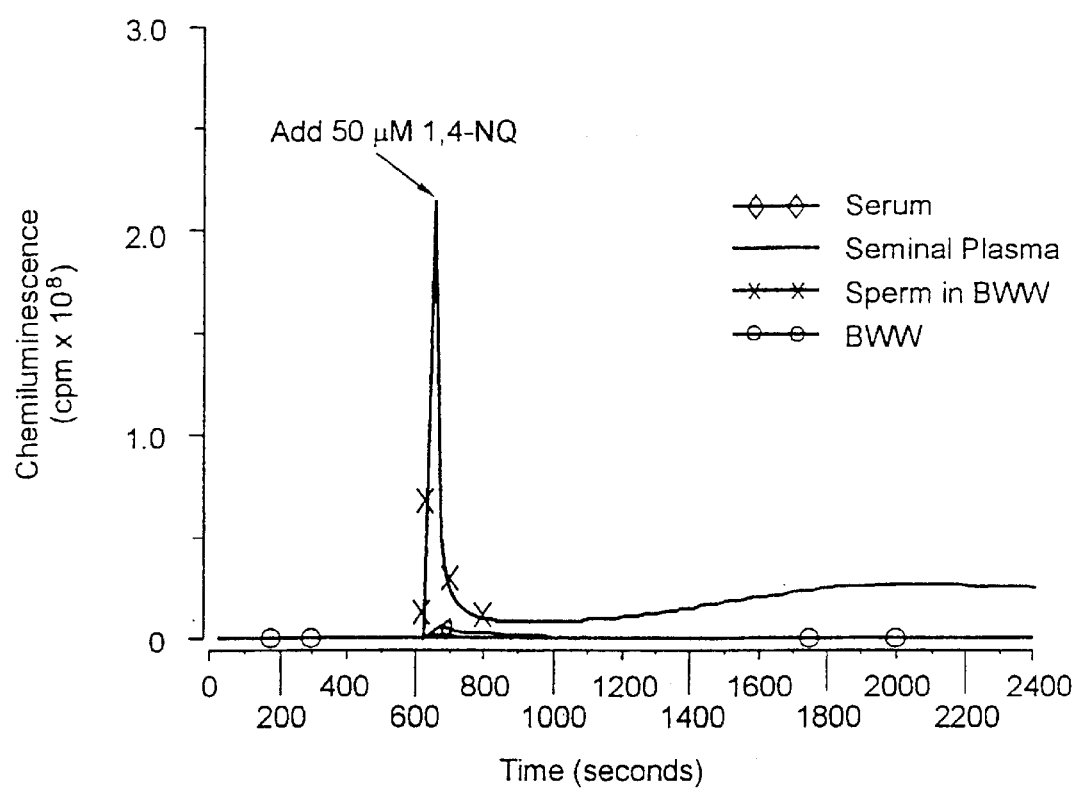
Figure 1C:
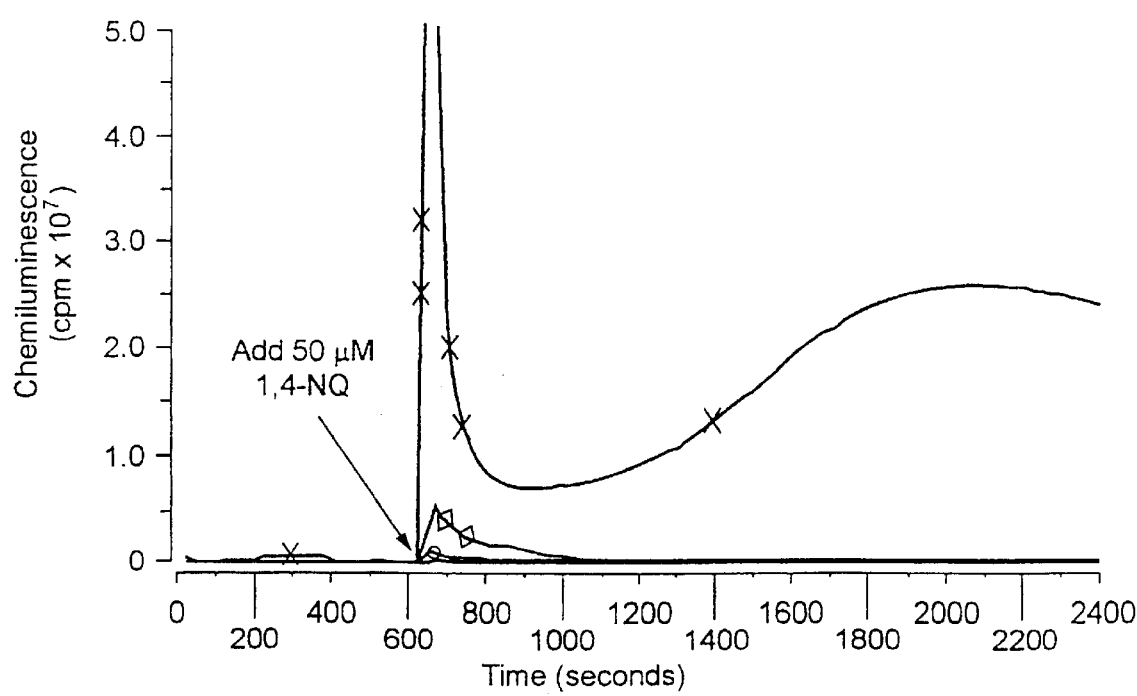

FIG. 1c. Chemiluminescence of 1,4-naphthoquinone induced superoxide production in serum, seminal plasma and sperm.

Figure 2:
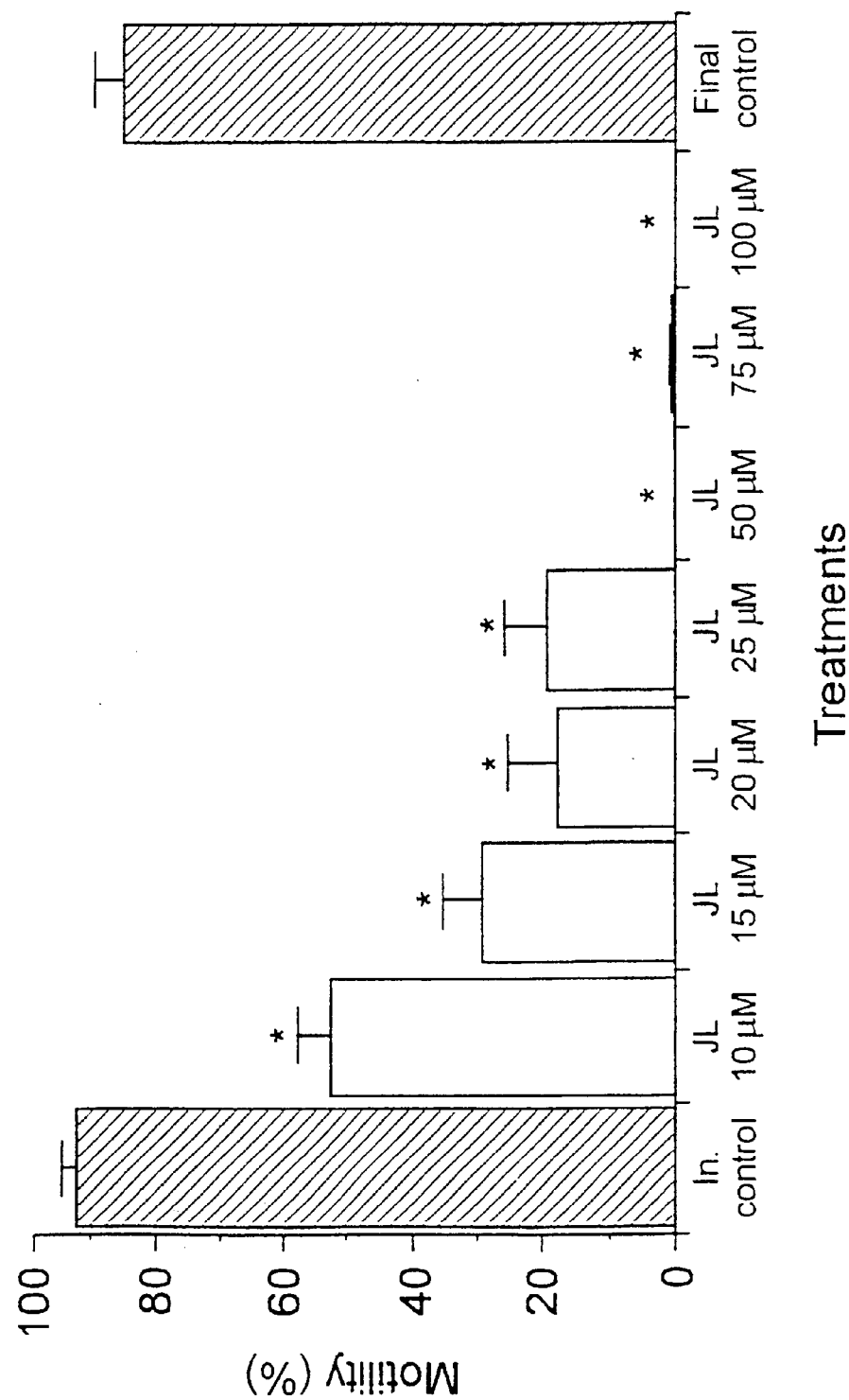

FIG. 2. Dose response of juglone on sperm motility.

Figure 3A:
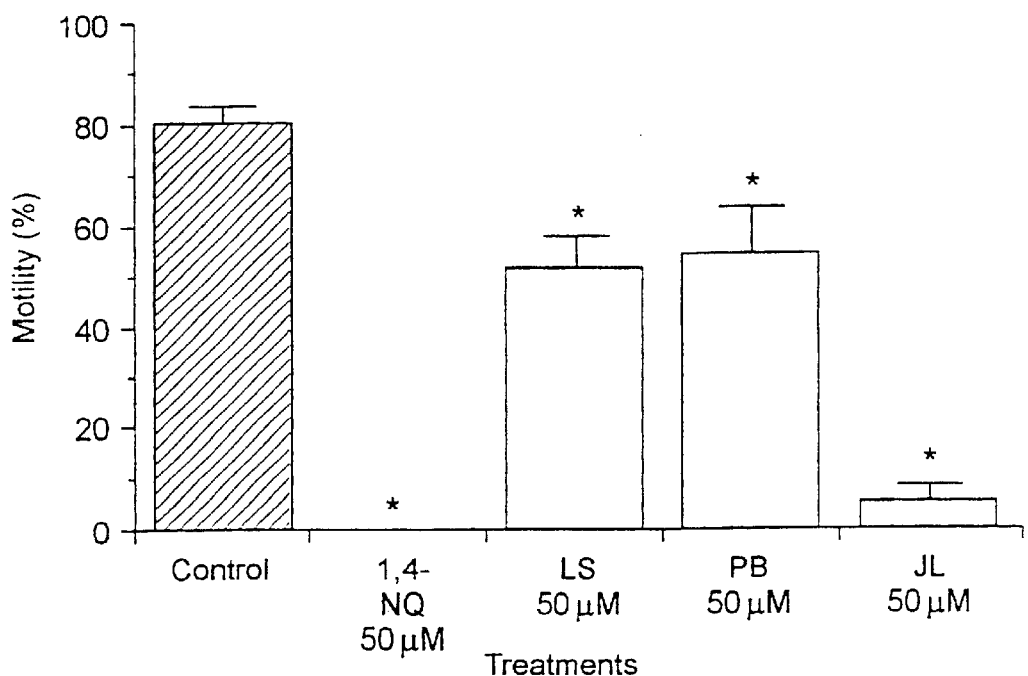

FIG. 3a. Effect of 50 $\mu$M 1,4-naphthoquinone, juglone, lawsone and plumbagin on the mean sperm motility of human sperm.

Figure 3B:
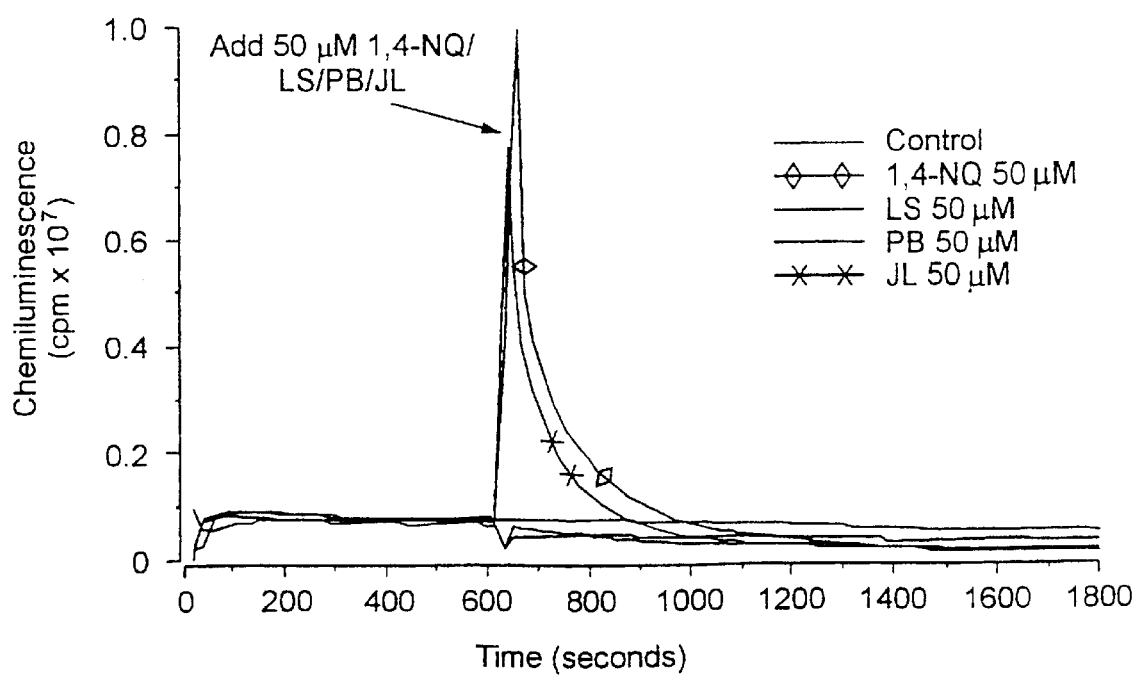

FIG. 3b. Effect of 50 $\mu$M 1,4-naphthoquinone, juglone, lawsone and plumbagin on superoxide production in sperm in seminal plasma.

Figure 4A:
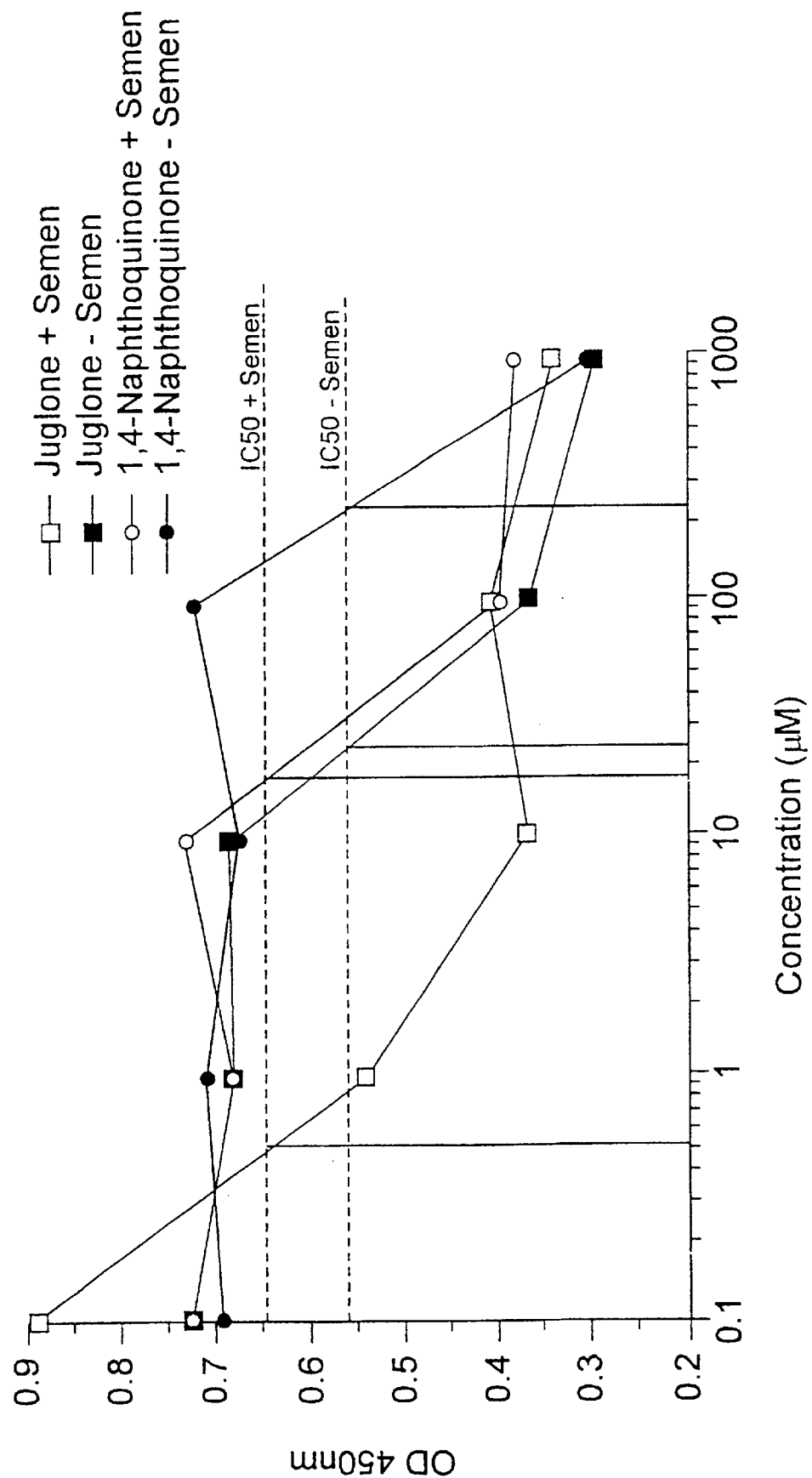
Figure 4B:
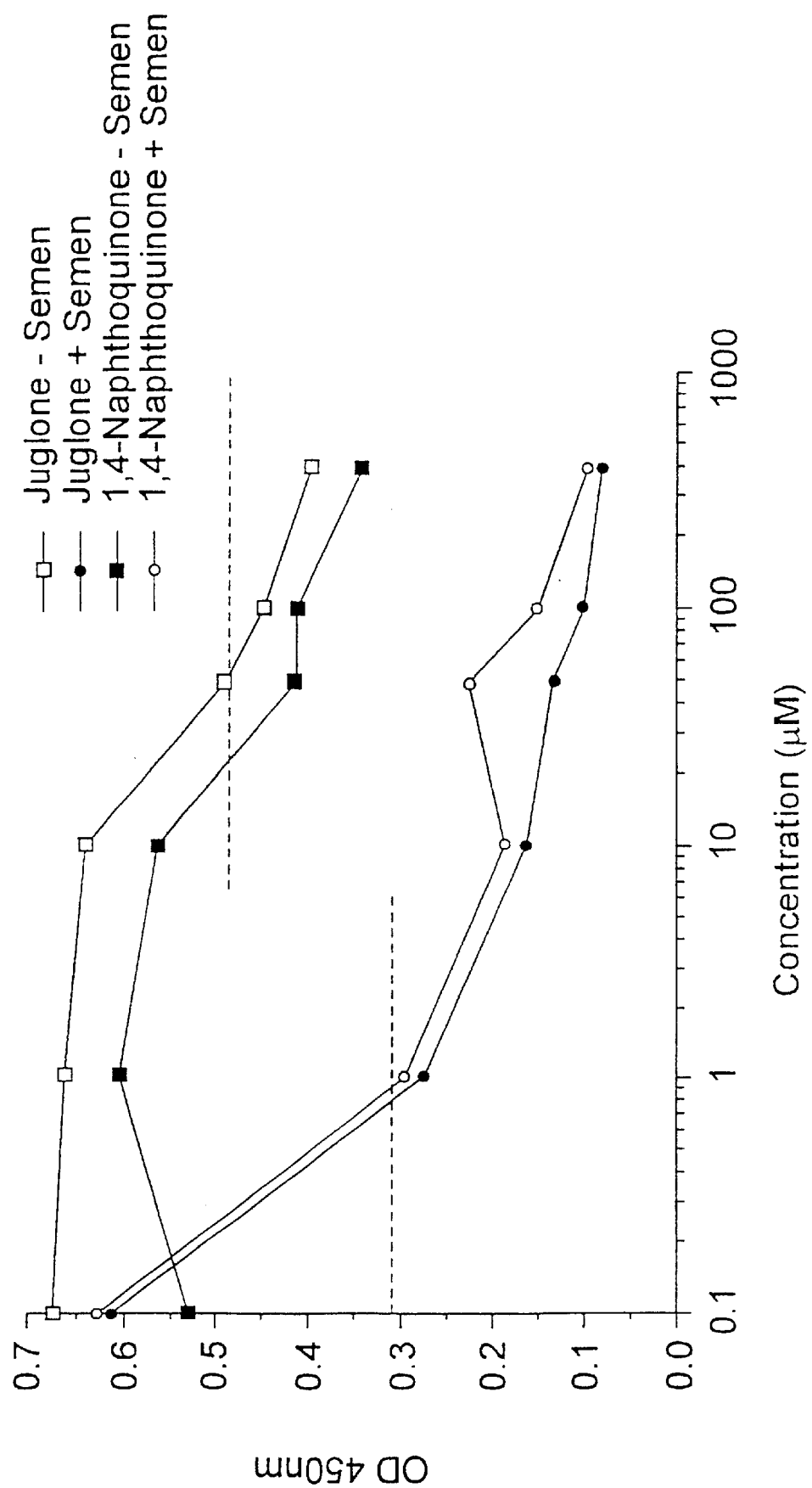

FIG. 4a, b. Antiviral activity of 1,4-naphthoquinone and juglone.

Figure 5A:
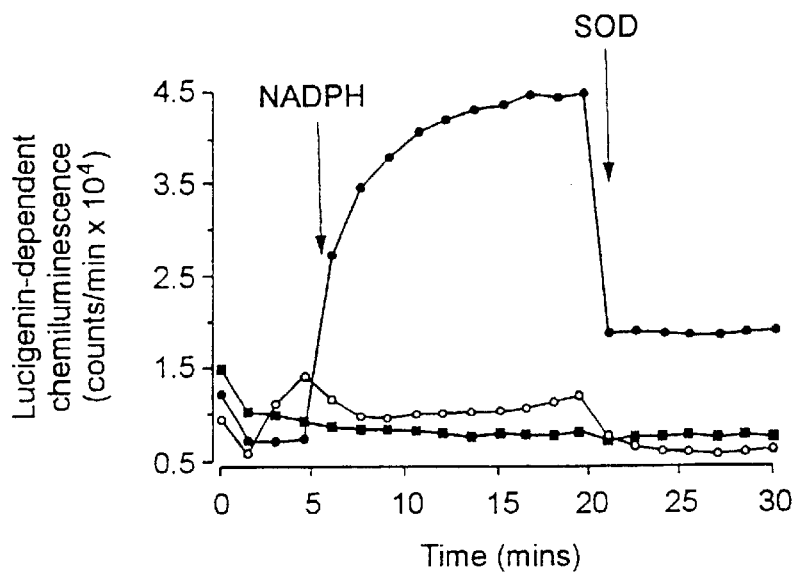

FIG. 5a. NADPH-induced superoxide anion generation by human spermatozoa. Addition of NADPH to the spermatozoa resulted in a 10 fold increase in the chemiluminescent signal (solid circles) but did not occur in controls lacking spermatozoa (solid squares) or containing vehicle alone (open circles); addition of SOD (18 U) led to an immediate quenching of the chemiluminescent signal.

Figure 5B:
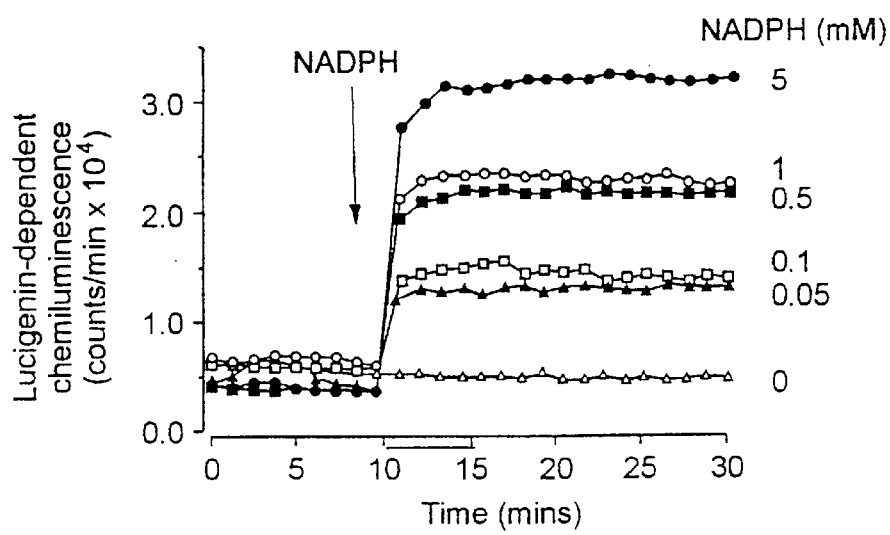
Figure 5C:
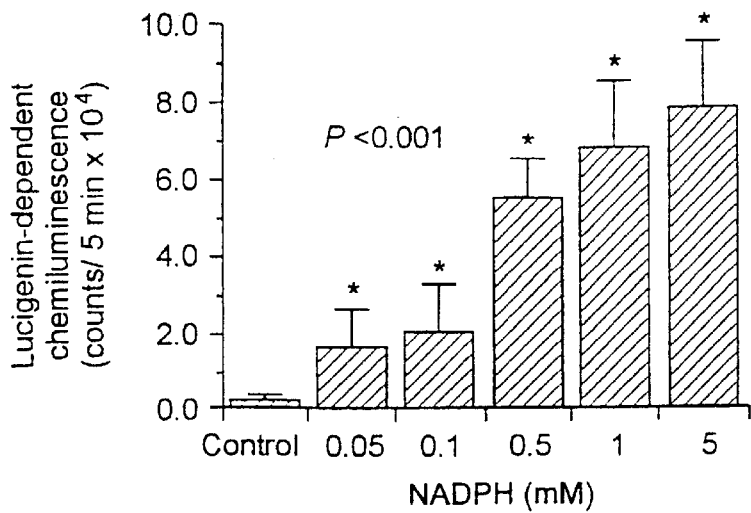

FIG. 5b. Dose-dependency of the NADPH induced response illustrated as continuous traces or FIG. 5c. as the mean levels of chemiluminescence, integrated over a 5 min period (solid bar), for 8 replicate experiments. Overall significance of dose effect was $P<0.001$; *$P<0.05$ compared with control by Fisher's PLSD.

Figure 6A:
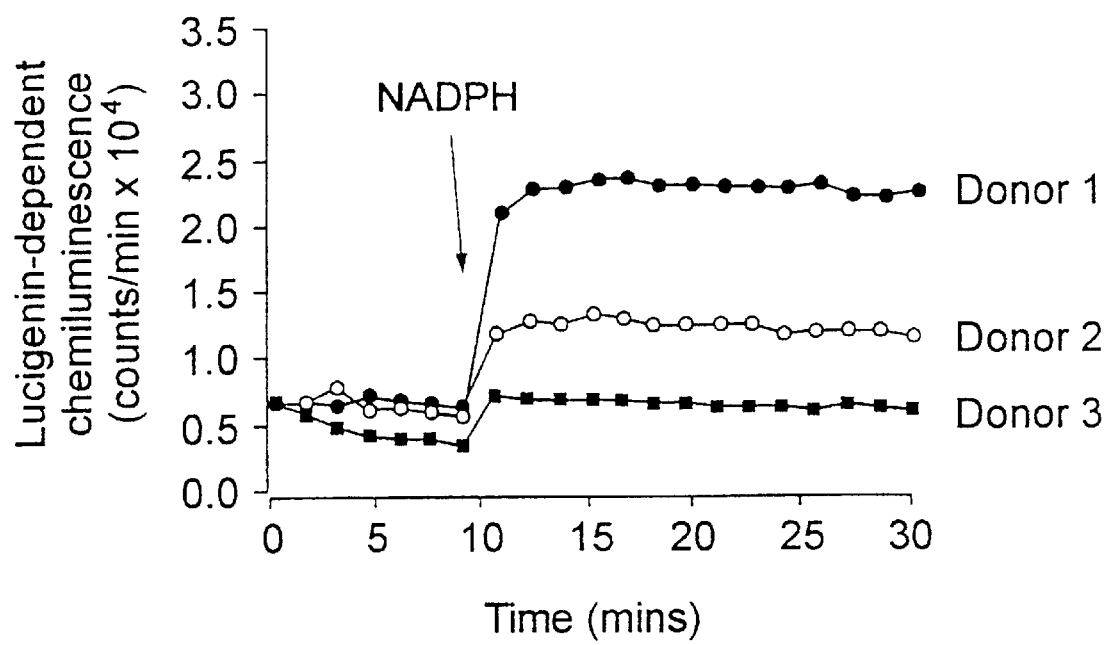
Figure 6B:
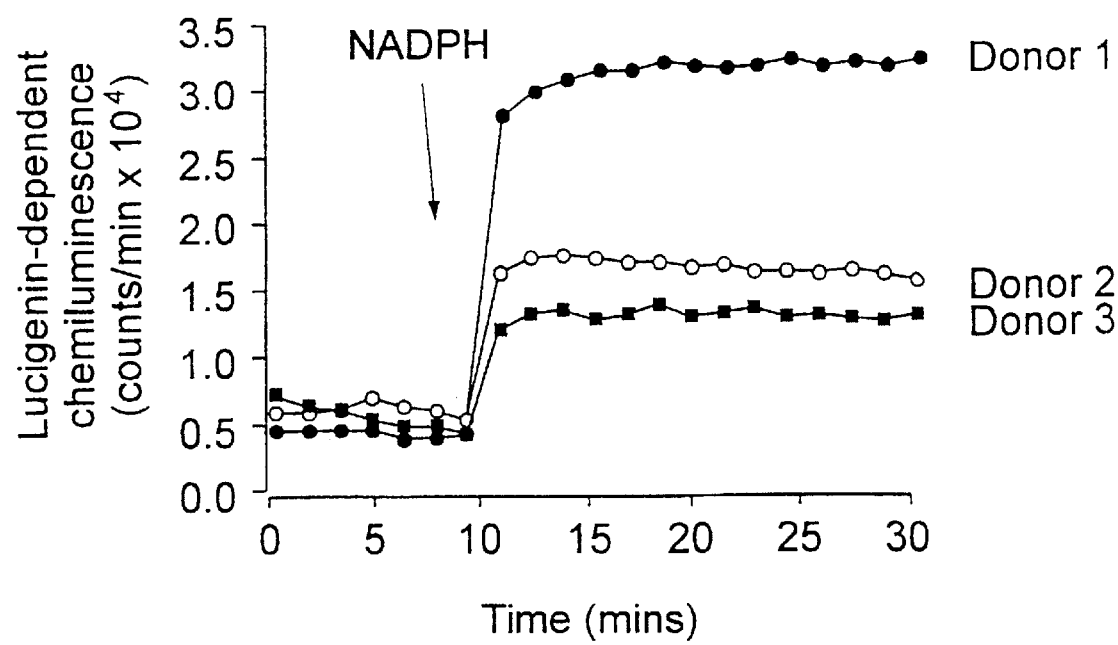

FIG. 6. Donor to donor variation in the levels of lucigenin-dependent chemiluminescence generated in response to a: 500 $\mu$M NADPH and b: 5 mM NADPH.

Figure 7A:
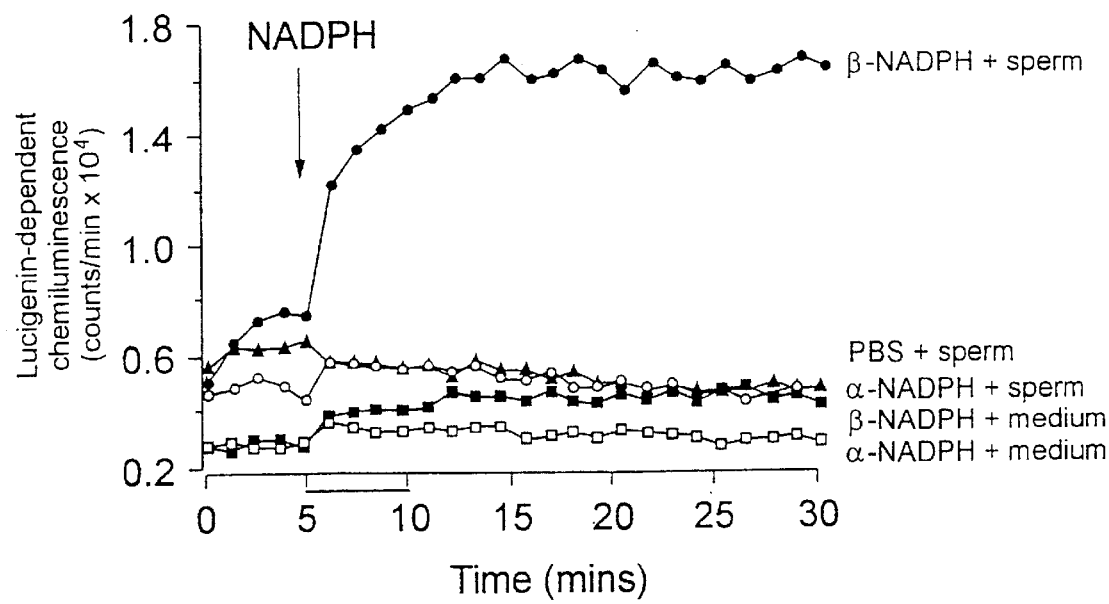
Figure 7B:
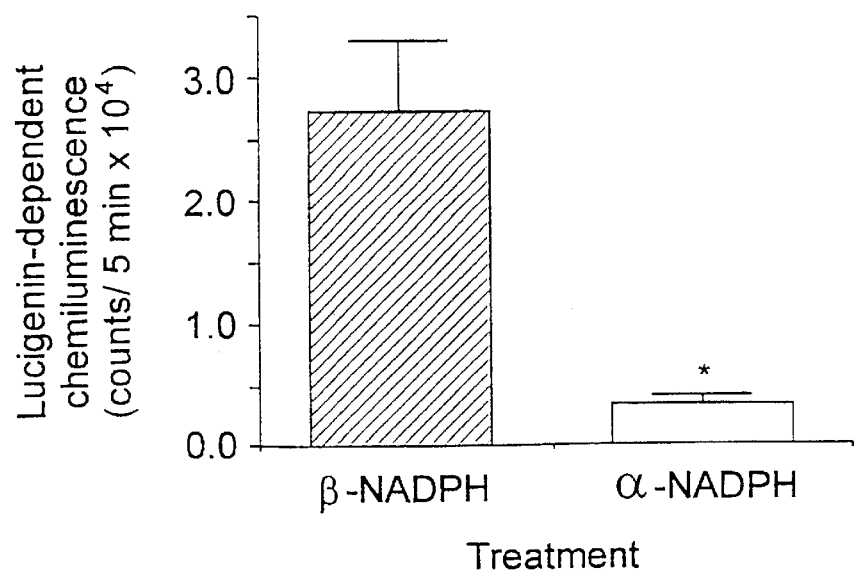

FIG. 7. Comparison of $\alpha$ and $\beta$ isomers of NADPH for their ability to induce chemiluminescent responses in human spermatozoa. a: longitudinal trace, solid circles illustrates the burst of ROS generation observed in response to 500 μM β NADPH, open circles shows lack of response to 500 μM α NADPH; open and closed squares are controls combining culture medium supplemented with α- and β NADPH, respectively while the triangles represent sperm suspensions treated with PBS vehicle alone. b: mean levels of chemiluminescence integrated over a 5 min period (solid bar) for 3 replicate experiments. *$P<0.05$ by Fisher's PLSD.

FIG. 8. Comparison of various nicotinamide adenine dinucleotides (500 μM) for their capacity to stimulate lucigenin-dependent chemiluminescent responses in human spermatozoa. a: representative longitudinal traces; solid and open circles represent responses to NADPH and NADH, while the solid and open squares illustrate the lack of response given by the $NADP^+$ and $NAD^+$ respectively. b: mean levels of chemiluminescence integrated over a 5 min period (solid bar) for 4 replicate experiments. $P<0.001$ for dose effect; *$P<0.05$ for comparisons with NADPH by Fisher's PLSD.

FIG. 9. Influence of various permeabilization and denaturation strategies on the generation of ROS by human spermatozoa in response to NADPH. a: representative longitudinal traces; solid squares illustrates the control response to NADPH which appears diminished because the scale on the y-axis has been expanded compared with previous figures. Repeated freeze-thawing resulted in a dramatic increase in the responsiveness of the spermatozoa to NADPH via mechanisms that could be suppressed by SOD (solid circles) or glutaraldehyde (open circles). Denaturation of the spermatozoa by heating to 57° C. for 30 min completely destroyed the ability of the spermatozoa to generate ROS in presence or absence of NADPH. b: mean levels of chemiluminescence integrated over a 5 min period (solid bar) for 3 replicate experiments, illustrating the beneficial effects of freeze-thawing on the NADPH response and the disruptive effects of denaturation with glutaraldehyde or heat. $P<0.001$ for overall treatment effect. *$P<0.05$ compared with NADPH control by Fisher's PLSD.

Figure 10A:
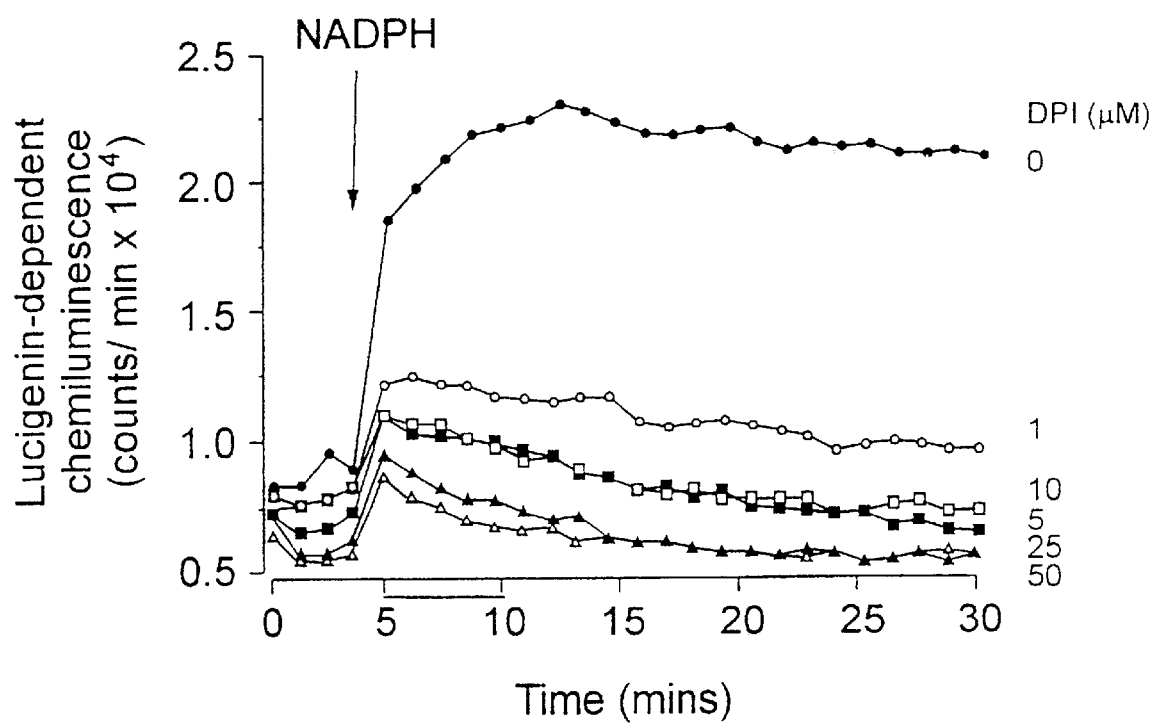
Figure 10B:
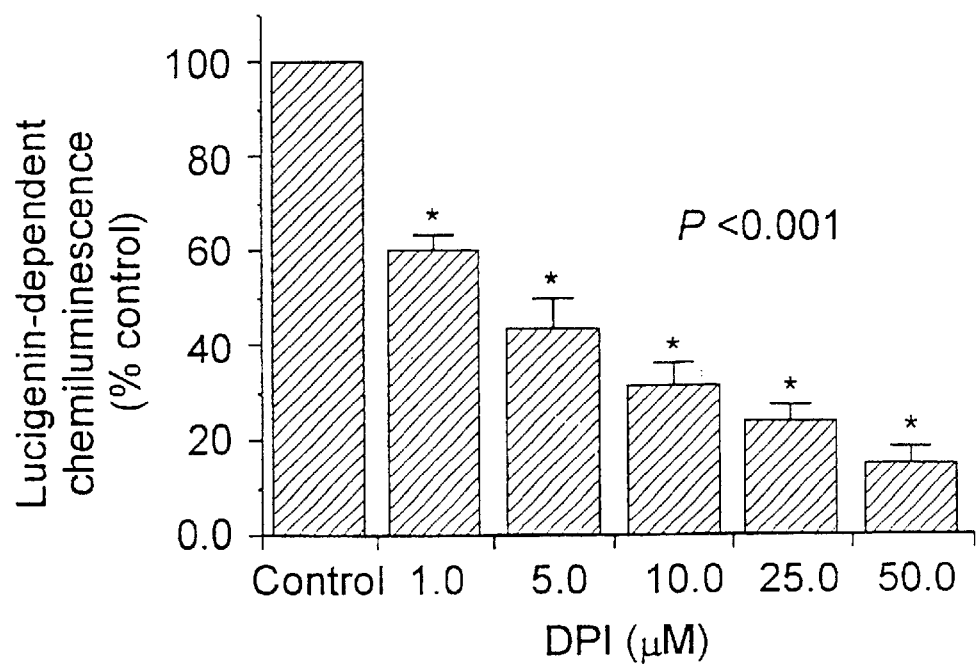

FIG. 10. Inhibitory effect of DPI on NADPH-induced, lucigenin-dependent, chemiluminescent responses of human spermatozoa. a: representative longitudinal traces illustrating control response (solid circles) and suppression with DPI at doses of 1 μM (open circles) 5 μM (solid squares) 10 μM (open squares) 25 μM (closed triangles) and 50 μM (open triangles) and b: mean levels of chemiluminescence integrated over a 5 min period (solid bar) for 7 replicate experiments. $P<0.001$ for overall effect of dose; *$P<0.05$ compared with NADPH control by Fisher's PLSD.

Figure 11A:
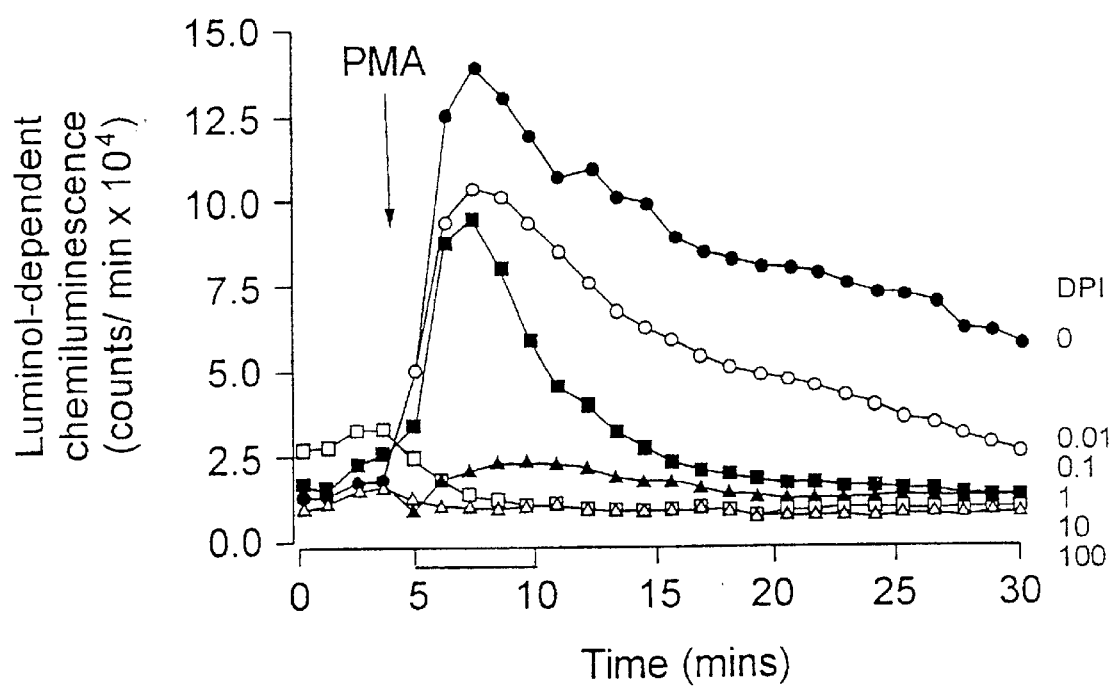
Figure 11B:
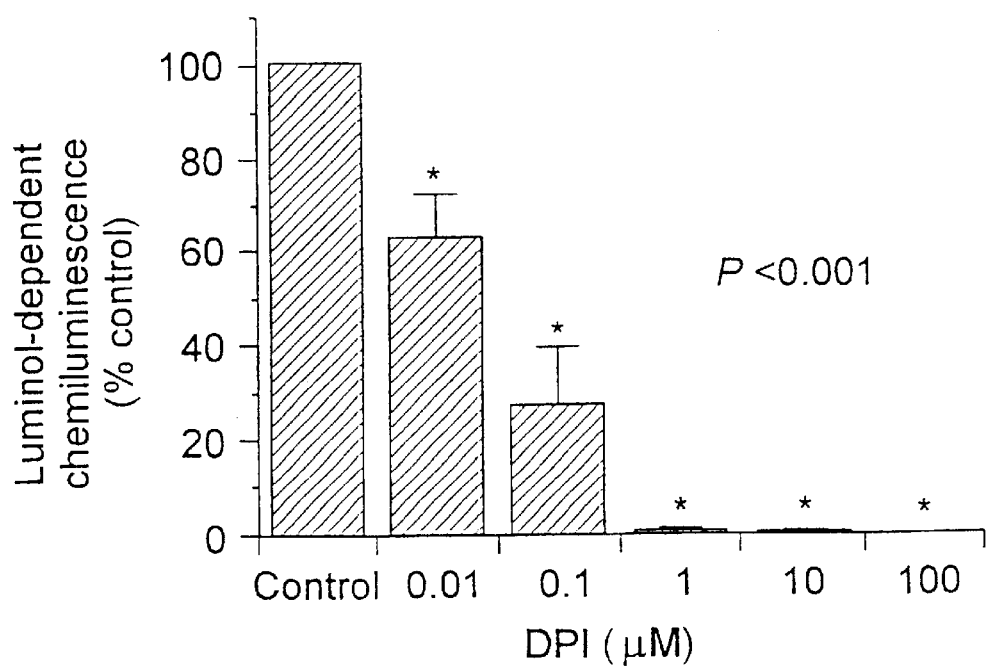

FIG. 11. Inhibitory effect of DPI on PMA-induced hydrogen peroxide production by human spermatozoa. a: representative longitudinal traces illustrating control response (solid circles) and dose-dependent suppression with DPI at doses of 0.01 μM (open circles), 0.1 μM (solid squares) 1 μM (open squares) 10 μM (solid triangles) and 100 μM (open triangles). b: mean levels of chemiluminescence integrated over a 5 min period (solid bar) for 4 replicate experiments. $P<0.001$ for overall effect of dose; *$P<0.05$ compared with PMA control by Fisher's PLSD.

FIG. 12. Inhibitory effect of quinacrine on the ability of human spermatozoa to generate ROS. a: Inhibitory effect of quinacrine on NADPH-induced, lucigenin-dependent, chemiluminescent responses of human spermatozoa. Representative longitudinal traces illustrating control response (solid circles) and suppression with quinacrine at doses 50 μM (open circles) 25 μM (solid squares) 10 μM (open squares) 5 μM (closed triangles) and 2.5 μM (open triangles) and b: mean levels of chemiluminescence integrated over a 5 min period (solid bar) for 3 replicate experiments, note lack of a clear dose response. $P<0.05$ for overall effect of dose; *$P<0.05$ compared with NADPH control by Fisher's PLSD. c: Inhibitory effect of quinacrine on PMA-induced hydrogen peroxide production by human spermatozoa. Representative longitudinal traces illustrating control response (solid circles) and dose-dependent suppression with quinacrine at doses of 10 μM (open circles), 25 μM (open squares) 50 μM (closed squares), 75 μM (solid triangles) and 100 μM (open triangles). d: Mean levels of chemiluminescence integrated over a 5 min period (solid bar) for 3 replicate experiments. $P<0.01$ for overall effect of dose; *$P<0.05$ compared with PMA control by Fisher's PLSD.

Materials and Methods

Reagents

All reagents were obtained from Sigma Chemical Company (St. Louis. Mo.), with the exception of Percoll (Pharmacia, Uppsala, Sweden), Dulbecco's phosphate-buffered saline (PBS), HEPES and medium 199 (Flow Laboratories, Irvine, Scotland), superoxide dismutase (SOD; bovine erythrocyte, 3910 U/mg, E.C.1.15.1.1) and A23187 (Novabiochem, Nottingham, England), glutaraldehyde (BDH Chemicals, Poole, Dorset, England) and the human serum albumin preparation, Albuminar (Immuno Ltd., Sevenoaks, England). Dynabeads (M-450 sheep anti-mouse IgG Dynabeads) were obtained from Dynal AS (Oslo, Norway) and the anti-common leukocyte antigen (CD45) monoclonal antibody was from the Scottish Antibodies Production Unit (Carluke, Scotland).

Sperm Preparation

Human semen samples were obtained from volunteer donors all of whom had been clinically examined and shown to be free of detectable pathology, including hepatitis and HIV infection. The semen samples were produced by masturbation, collected into sterile, plastic containers and transported immediately to the laboratory for subsequent analysis and experimentation. Each semen sample was allowed to liquefy for at least 30 min, before conducting a routine semen analysis to confirm the normozoospermic status of the material (World Health Organization, 1992).

The spermatozoa were subsequently isolated from seminal plasma on a two step discontinuous Percoll gradient, as described by Aitken and Clarkson (1988). The isotonic Percoll used in the gradient was created by supplementing 90 ml of Percoll with 10 ml of 10× concentrated medium 199, 1.5 ml 20% Albuminar, 3 mg sodium pyruvate, 0.37 ml sodium lactate, and 200 mg sodium hydrogen carbonate. This isotonic Percoll preparation was designated 100% Percoll (Lessley and Garner,1983) and a 50% preparation was made by diluting it 1:1 with HEPES-buffered medium Biggers Whitten Whittingham (hereinafter called "BWW") (Biggers et al., 1971), supplemented with 0.3% Albuminar. The gradient used for sperm preparation consisted of 3 ml of 100% Percoll overlaid with 3 ml of 50% Percoll in a sterile 15 ml conical-bottomed centrifuge tube. Liquefied semen (1–3 ml) was carefully laid on the top of each gradient and the whole preparation was centrifuged for 20 min at 500 g. After centrifugation, the seminal plasma was discarded and the cell population pelleting at the base of the 100% Percoll was collected, washed with approximately 10 ml of BWW, centrifuged at 500 g for 5 min and finally resuspended in BWW at a sperm concentration of $20 \times 10^6$/ml. Purified preparations of human sperm plasma membrane were prepared by a combination of sonication and sucrose gradient ultracentrifugation as described by Aitken, Hulme et al. (1987).

Assessment and Removal of Contaminating Leukocytes

The presence of leukocytes in the suspensions of spermatozoa was evaluated by employing a sensitive leukocyte provocation test, involving the chemotactic peptide N-formyl-methionyl-leucyl-phenylalanine (FMLP) and a chemiluminescent detection system as described by Krausz et al. (1992). Cell suspensions that responded positively to the FMLP challenge test were either not used in further assays, or were subjected to the following protocol to remove the contaminating leukocytes. Leukocyte removal was accomplished via a magnetic cell separation technique (Krausz et al., 1992) involving the use of magnetic M-450 Dynabeads™ coated with sheep anti-mouse immunoglobulin G and an anti-CD 45 monoclonal antibody. A 40 $\mu$l aliquot of labelled Dynabeads was added to 1 ml of sperm suspension and incubated on a slowly rotating wheel for 30–60 min, at room temperature. After this time, the Dynabeads and adherent leukocytes were removed by the means of a magnet and the remaining cell suspension re-challenged with FMLP to determine whether the procedure had been successful. The leukocyte removal procedure was repeated until the sperm suspension failed to give a chemiluminscent response to FMLP.

The Effect of Quinones on Sperm Motility

Following the preparation of spermatozoa by standard Percoll gradient they were resuspended in homologous seminal plasma to a concentration of 20 million per ml, immediately prior to the beginning of the experiment. 50 $\mu$l of the sperm suspension was placed in an eppendorf tube, and the quinone was either added alone or in combination with other reagents, for example, KI, HRP (Horseradish Peroxidase), BHT (butylated hydroxytoluene) etc. depending on the experiment. The volume was made up to 100 $\mu$l with BWW/PVA.

The quinone was always the final reagent to be added. For example when reagents such as HRP and BHT were included in the experiment, BWW/PVA would be added to the sperm in seminal plasma first followed by BHT, HRP and finally the quinone, i.e. the reagents thought to be the most active in regards to their effect on spermatozoa were added finally. The sample was gently agitated and 10 $\mu$l was placed on a slide and a motility was scored. The aim was to score a motility approximately 20 seconds following the addition of the quinone. There were two controls set up, one motility count taken at the beginning of the experiment (initial control) and one motility count taken at the end of the experiment (final control). The controls consisted of 50 $\mu$l of the sperm suspension followed by the addition of 50 $\mu$l BWW/PVA. The reason for having two controls was to observe if any changes in sperm motility had occurred simply as a factor of time, i.e. from residing in seminal plasma for a long duration. At all times during the experiment, the spermatozoa were incubated in a hot box at 24° C. All motility experiments were carried out on sperm suspended in seminal plasma unless otherwise stated.

Detection of Reactive Oxygen Species Generation

ROS generation was monitored by luminometry employing the chemiluminescence probes lucigenin and luminol. Lucigenin is sensitive to the presence of superoxide anion and was used to monitor the free radical responses to NAD(P)H. Luminol, when used in conjunction with horseradish peroxidase (HRP; Sigma Type VI, 288 U/mg), detects mainly hydrogen peroxide (Aitken et al., 1992) and was used to monitor the responses of spermatozoa to PMA (phorbol 12-myristate, 13-acetate), an activator of protein kinase C. NAD(P)H could not be used with the luminol-peroxidase system because of the generation of high background signals, presumably due to the oxidase reactions of HRP. Photon emission was monitored at 37° C. using the Bermold 9505B luminometer (Berthold, Wilbad, Germany) featuring 6 electronically compensated, peltier cooled, photomultipliers and the results expressed as counts/minute. For both of the probes used, 400 $\mu$l of spermatozoa, at a concentration of $10 \times 10^6$/ml, were placed in a 3 ml plastic, flat-bottomed plastic tube. For luminol-based reactions, the spermatozoa were suspended in BWW supplemented with Albuminar, but when lucigenin was used the Albuminar was replaced with 1 mg/ml polyvinyl alcohol. A 4 $\mu$l aliquot of a 25 mM stock solution of either luminol or lucigenin m-dimethyl sulphoxide (DMSO), was then added to the cell suspension, resulting in a final probe concentration of 250 $\mu$M. For the measurement of hydrogen peroxide generation by intact cells, luminol-dependent chemiluminescence was enhanced by addition of 8 $\mu$l of HRP, freshly prepared at a concentration of 2 mg/ml in PBS, to give a final HRP concentration of 11.52 U/ml. The luminometer results were recorded as continuous traces and as integrated photon counts over a fixed period of time (5 min).

Detection of Superoxide ($O_2^-$)

Lucigenin is used in the detection of $O_2^-$. It is a charged compound and therefore cannot permeate the cell membrane, and thus measures the production of superoxide extracellularly. The spermatozoa were prepared by standard Percoll gradient and resuspended in homologous or pooled seminal plasma (depending on availability of homologous seminal plasma), to a concentration of 10 million per ml. Occasionally the spermatozoa were resuspended in BWW/PVA according to the experimental design. 400 $\mu$l of the sperm suspension was pipetted into each plastic tube. 4 $\mu$l of 25 mM lucigenin was then added to each tube, and after the checking and removal of any bubbles, the tubes were immediately processed for luminometry. It was possible to stop the run at any time, so that reagents such as quinones could be added, without affecting the results.

Detection of $H_2O_2$

Luminol alone measures $H_2O_2$; however when used alongside HRP, it can measure the production of $H_2O_2$ internally and externally. The sperm were prepared by standard percoll gradient and resuspended in seminal plasma or BWW/PVA to a concentration of 10 million cells per ml. 400 $\mu$l of sperm suspension was pipetted into each plastic tube as before, and 8 $\mu$l of HRP (2 mg/ml BWW/PVA) was carefully added to each tube, followed by 4 $\mu$l of 25 mM luminol. Each tube was then placed into a channel and the run was started. The run was temporarily stopped to make further additions of reagents such as quinones.

Nicotinamide Adenine Dinucleotide Phosphate (NADPH) Induced ROS

The ability of human spermatozoa to generate superoxide anion in response to NADPH was monitored by lucigenin-dependent chemiluminescence and compared with its non-phosphorylated and non-reduced counterparts, i.e. NADH, $NADP^+$ and $NAD^+$. In addition, the stimulatory properties of an isomer of NADPH, usually non-active in reductive biosynthesis, were examined. All pyridine nucleotides were made up to the required concentration in PBS immediately prior to use. Stock solutions of the nucleotides were made up at concentrations 10 fold higher than the required final working concentration, to allow for a 10 fold dilution on addition to the suspensions of spermatozoa.

Impact of Cell Viability on NADPH-induced Superoxide Anion Generation by Human Spermatozoa The impact of cell viability on NADPH-induced ROS generation was examined by subjecting these cells to 3 cycles of freeze-thawing using dry ice and methanol to effect the rapid cooling of the cells to around −20° C. Suspensions of human spermatozoa were also denatured by heating the cells to 57° C. for 30 min or fixation in 0.25% glutaraldehyde, before being centrifuged (500 g for 5 min) and resuspended in fresh medium for the assessment of lucigenin-dependent chemiluminescence following exposure to 500 µM NADPH.

Effect of DPI on ROS Generation

DPI (Diphenylene Iodonium; a flavoprotein inhibitor) was dissolved in 10% DMSO to give a 10 mM stock solution, aliquots of which were stored at −20° C. until use. In all experiments, DPI was added to the spermatozoa before the addition of NADPH or PMA while control incubations were supplemented with DMSO alone. ROS generation was recorded for approximately 10 min to establish a steady state signal and then 45 µl of NADPH (final concentration 500 µM) or 4 µl of PMA (final concentration 100 nM) were added and the responses monitored for around 20 min using lucigenin and luminol-peroxidase based chemiluminescence respectively.

Effect of Quinacrine on ROS Generation

Quinacrine was purchased from Sigma and dissolved in 10% DMSO to give a stock solution of 10 mM. In dose-dependent studies 4 µl aliquots of quinacrine were added to 400 µl of spermatozoa to give final concentrations of 2.5, 5, 10, 50, 75 and 100 µM respectively, control incubations receiving the DMSO vehicle alone. The impact of quinacrine on NADPH- and PMA-induced ROS generation was monitored as described above for DPI.

Quantification of Superoxide Anion Generation

Superoxide anion generation was quantified spectrophotometrically via the superoxide-dependent reduction of cytochrome C (McCord and Fridovich, 1969). Spermatozoa were used at an increased concentration of $10 \times 10^7$/ml in BWW supplemented with PVA (1 mg/ml). An aliquot (400 µl) of this sperm suspension was placed in a 1 ml disposable, plastic cuvette and 50 µl of cytochrome C (Type VI from horse heart), was added to give a final working concentration of 100 µM. The reference cuvette contained the same ingredients, except that 50 µl of SOD was added to give final concentration of 196 U/ml. Absorbance was monitored at 550 nm and the SOD-inhibitable superoxide generation calculated using an extinction coefficient for reduced cytochrome C of $\epsilon=21.1$ mM$^{-1}$cm$^{-1}$.

Statistics

Each experiment was replicated at least 3 times and the results were analyzed by one way analysis of variance (ANOVA) with repeated measures using the Statview programme (Abacus Concepts, Berkeley, Calif.) on an Apple Macintosh Centris 650 computer. Differences between individual groups were examined with Fisher's PLSD test with the significance threshold set at $P<0.05$.

Assay for Determining Virucidal Activity Using Cell-Free Viruses

A simple, microtitre plate assay was developed (viral adhesion assay) in which the virus was attached to the solid phase by Pol-L-lysine Hydrobromide (PLL, Sigma). Sterile 24 and 96 well plates (Nunc) were coated for 1 hour with 50 µl of 50 µg/ml PLL at room temperature. When using 96 well microtitre plates the outer ring of wells were left uncoated and filled with 250 µl of sterile PBS to counteract the effects of evaporation. The coated wells were washed twice with sterile PBS using a Denley-4 plate washer. 25 µl of RPMI 1640 medium containing HIV-1 (50×TCID$_{50}$) was added to the wells and incubated for 1 hour at room temperature. The plate was again washed twice with sterile PBS. 25 µl of varying concentrations of the candidate virucide were added to each well for 15 minutes and the virucide removed with two washes of sterile PBS. The T-lymphocyte cell line C8166, at a concentration of $4 \times 10^4$ cells in 300Fl RPMI 1640, were added to each well so that the cells formed a uniform monolayer on the adherent virus. After incubation for 72 hours, the number of syncytia in the monolayer gave an accurate measure of the amount of infectious virus present. Wells untreated with virucide were used as positive controls. All solutions and incubation stages involving virus/virucide interactions were maintained at 37° C. The assay allowed the efficient removal of the candidate virucides or disinfectant and allowed the compound to be assessed for accurately determined contact times.

Results

Evaluation of the Effects of 1,4 naphthoquinone (NQ) on Sperm Motility and ROS Generation in Sperm, Seminal Plasma and Serum FIG. 1a shows that 1,4-napthoquinone produces a dose-dependent inhibition of sperm motility with an approximate ID$_{50}$ of 10 µM. All of the treatments significantly reduced sperm motility compared to the controls and there was no significant difference between the initial and final control. Spermatozoa exposed to 1,4-naphthoquinone concentrations ranging from 25 µM to 100 µM were completely immobilised.

FIG. 1b shows the superoxide burst generated by spermatozoa in seminal plasma, in response to the addition of 1,4-naphthoquinone. Increasing doses of this compound led to a corresponding increase in superoxide production. The superoxide induced was generally a rapid burst that declined within approximately one hundred seconds. It was evident that the spike of superoxide activity representative of 50 µM 1,4-naphthoquinone was much greater than that induced by the 25 µM dose. However, by referring back to FIG. 1a, it can be seen that 25 µM 1,4-naphthoquinone was capable of immobilising spermatozoa to the same extent as 50 µM 1,4-naphthoquinone, thus indicating that such elevated amounts of superoxide were not required to impair sperm motility.

Superoxide generation was also observed in seminal plasma in the absence of spermatozoa. However, the amount of superoxide produced was reduced compared to when spermatozoa were present, although the pattern of the superoxide generation was the same.

To evaluate the capacity of 1,4 naphthoquinone to induce $H_2O_2$ production in sperm, seminal plasma and serum, luminol/peroxidase-dependent chemiluminescence was used (FIG. 1c). A concentration of 50 µM 1,4-naphthoquinone was selected for this experiment as it consistently induced high levels of ROS. Spermatozoa in BWW gave an instantaneous significant burst of $H_2O_2$ on addition of the reagent, followed by a slow secondary increase in $H_2O_2$, that peaked approximately 25–30 minutes after the initial exposure to 1,4-naphthoquinone. Seminal plasma and serum displayed no such activity in response to this compound. They responded initially to the addition of 1,4-naphthoquinone, but insignificantly in comparison with sperm in BWW. This response also declined to basal levels fairly quickly (approximately 200–300 seconds). The BWW control did not respond at all to the addition of 1,4-naphthoquinone (FIG. 1c).

The effect of 1,4-naphthoquinone on lipid peroxidation was also evaluated. The results demonstrated that lipid peroxidation did not occur in spermatozoa as a consequence of exposure to 1,4-naphthoquinone. None of the treatments were significantly different to the control (no 1,4-naphthoquinone).

Effect of Juglone on Human Sperm Motility

Juglone produced a dose-dependent inhibition of sperm motility with an $ID_{50}$ of approximately 10 μM (FIG. 2). The maximal spermicidal effect was achieved using 50 μM juglone which completely immobilised sperm.

Evaluation of the Effects of Different Quinones on Sperm Motility and Superoxide Generation in Human Sperm Spermicidal efficacy is quinone-dependent. 1,4-naphthoquinone, juglone, lawsone and plumbagin, 50 μM in all cases, significantly reduced sperm motility compared to control, but only 1,4-naphthoquinone and juglone severely inhibited sperm motility (see FIG. 3a). The mean motility scores for lawsone and plumbagin were 51% and 54% respectively, whereas the mean motility scores for 1,4-naphthoquinone and juglone were 0.143% and 5% respectively. The capacity of the aforementioned quinones to induce superoxide production in sperm correlated with the motility score data (see FIG. 3b).

Evaluation of the Antiviral Effects of 1,4-naphthoquinone and Juglone

The antiviral actions of 1,4-naphthoquinone and juglone against HIV-1 were assessed in the presence and absence of human semen (see FIGS. 4a, b). In the absence of semen both compounds exhibited dose-dependent antiviral activity. However, in the presence of semen this antiviral activity is potentiated by an order of magnitude.

Induction of Superoxide Anion Generation with NADPH

Human spermatozoa rapidly generated a lucigenin-dependent chemiluminescent response on addition of exogenous NADPH to the culture medium (FIG. 5a). This signal reached a plateau within 5 to 10 min and then remained constant for at least 3 hr. Over this time period the percentage motility of the spermatozoa remained unchanged with doses of NADPH ranging from 0.625 to 10 mM. The NADPH-induced signal was quenched upon addition of SOD (FIG. 5a) emphasizing the importance of superoxide anion in the development of the chemiluminescent signal. The latter also exhibited a clear linear dependence on extracellular NADPH concentration (FIGS. 5b, 5c) although a Km value could not be calculated for this activity as no substrate saturation effect was observed at NADPH doses up to 2M. Another feature of the response to NADPH, which may have clinical relevance, was that the magnitude of the chemiluminescent signal varied considerably from donor to donor, as illustrated in FIGS. 6a, b.

To confirm that a substrate specific, enzymatic mechanism was involved when human spermatozoa were induced to generate superoxide with exogenous NADPH, the abilities of the two optical isomers of NADPH to stimulate this activity were compared. This analysis revealed that only the β isomer, which is the form of NADPH that participates in enzymatic, reductive biosynthesis, significantly induced superoxide anion generation, the a isomer was without effect (FIGS. 7a, b).

Figure 8A:
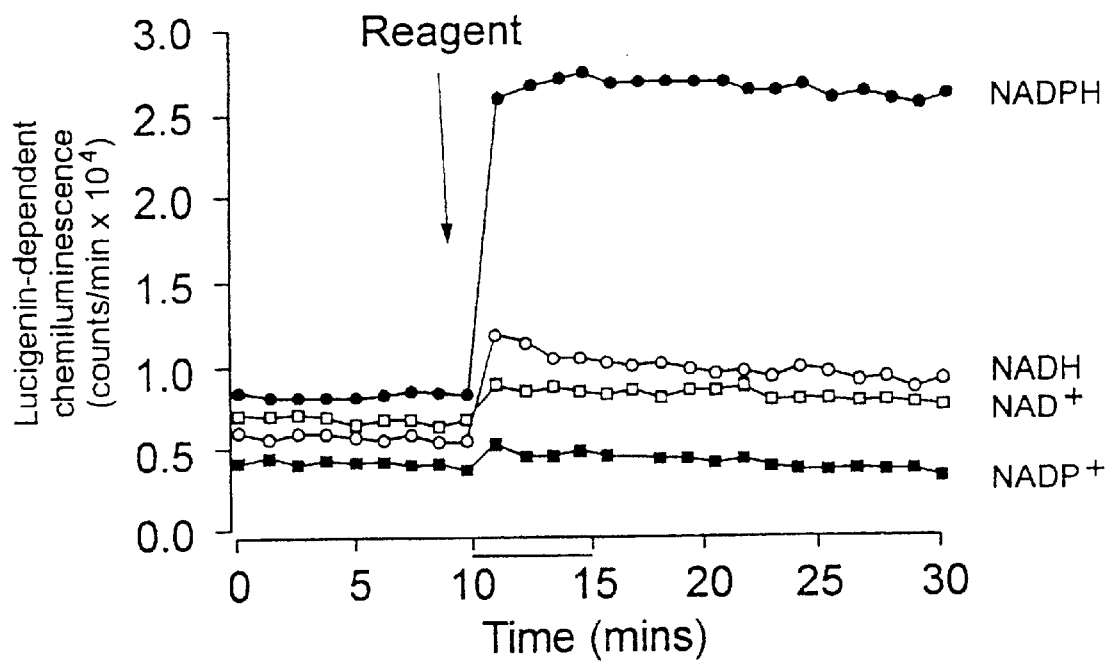
Figure 8B:
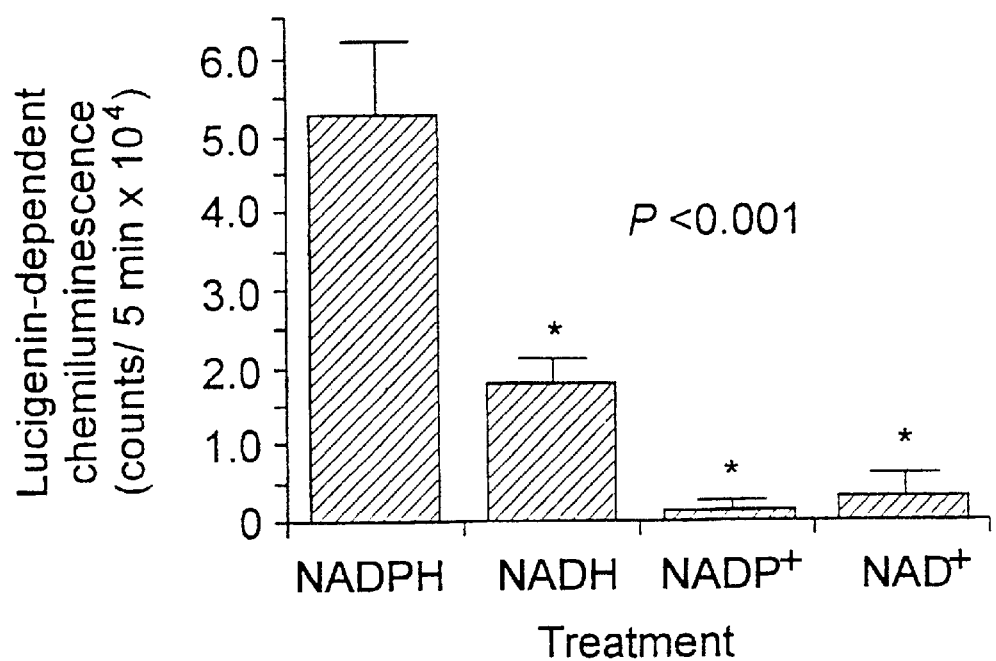

To further examine the specificity of the response to exogenous NADPH, the abilities of nonphosphorylated and non-reduced nicotinamide dinucleotides to stimulate superoxide anion generation by human spermatozoa were also investigated (FIGS. 8a, b). NADH reduced superoxide anion generation by the spermatozoa but at a level approximately one third of that induced by β-NADPH, while $NADP^+$ and $NAD^+$ were almost completely without effect. Statistical analysis of the group data revealed that the ability of NADPH to induce a lucigenin-dependent chemiluminescent response was significantly greater than any other nicotinamide dinucleotide derivative assessed (P<0.001; FIG. 8b).

Quantification of Superoxide Anion Generation

Unstimulated human spermatozoa in the medium BWW were characterized by a low, steady state level of superoxide anion production (1.51+0.71 pmol.min$^{-1}$. $10^6$ spermatozoa) as determined spectrophotometrically by the SOD-inhibitable reduction of ferricytochrome C. The addition of 2 mM NADPH resulted in a sudden burst of superoxide generation during which the reaction rate accelerated dramatically to 99.52+/-9.12 pmol.min$^{-1}$. $10^6$ spermatozoa. Thereafter the rate at which superoxide was released into me medium stabilized at 7.65+/-0.97 pmol.min$^{-1}$. $10^6$ spermatozoa (n=5).

Membrane Integrity and ROS Generation

Figure 9A:
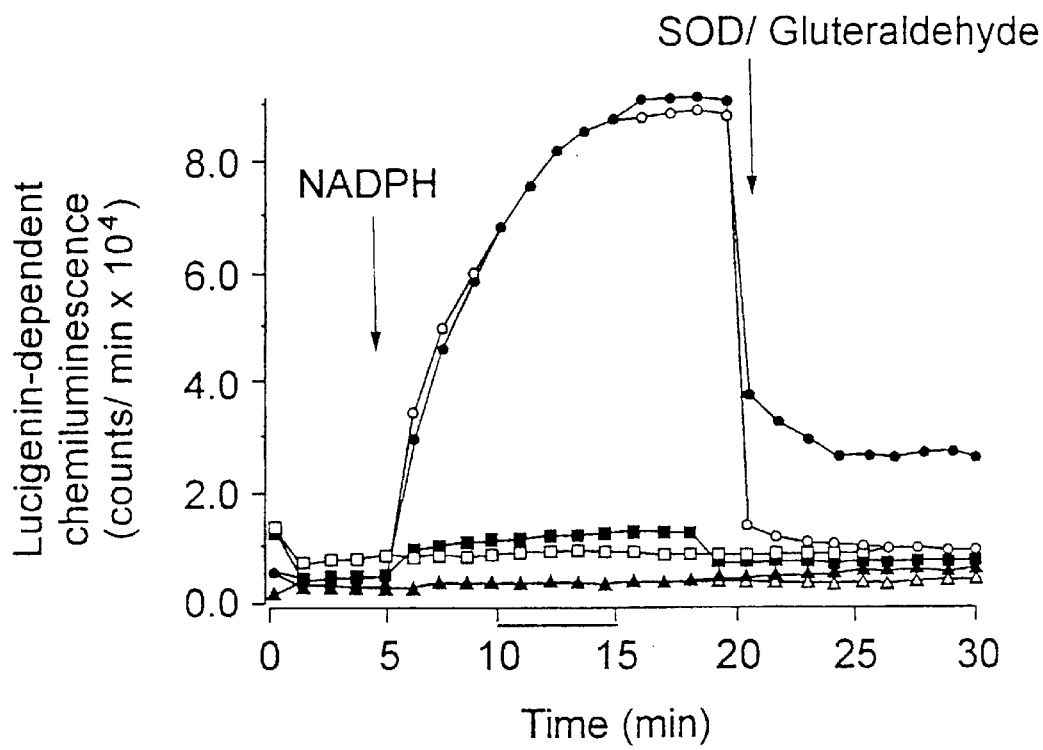
Figure 9B:
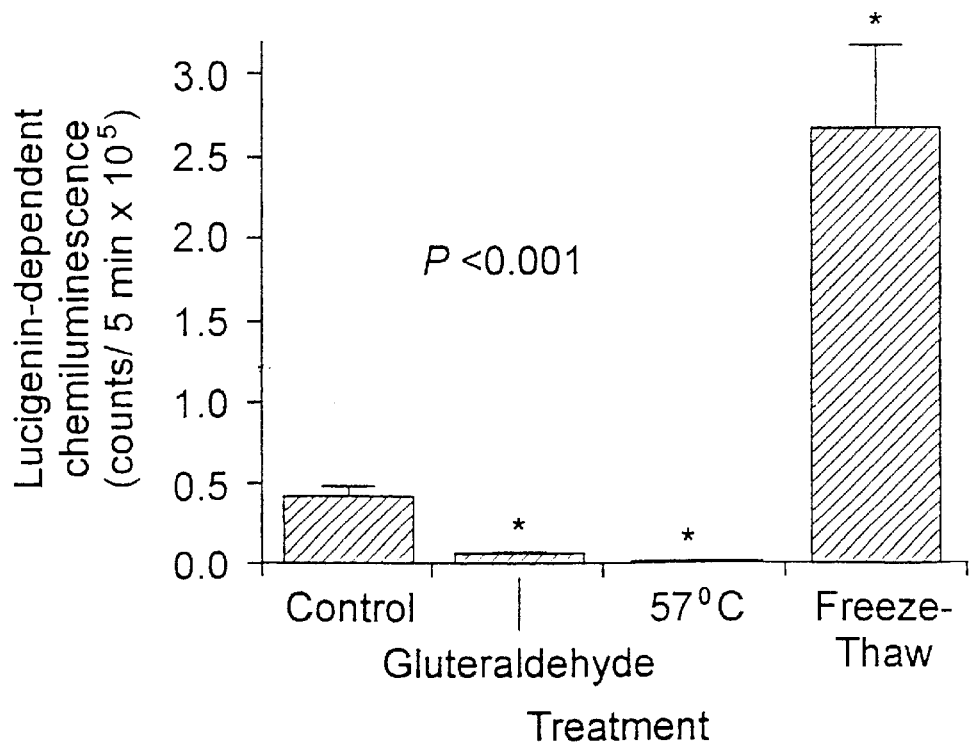

The impact of membrane integrity on exogenous NADPH-induced superoxide generation by human spermatozoa was investigated by subjecting these cells to repeated cycles of freeze-thawing prior to the addition of reduced dinucleotide. Far from inhibiting NADPH-induced superoxide generation, this treatment increased the responsiveness of human spermatozoa to exogenous NADPH approximately 9-fold, compared with control incubations maintained at 37° C. (FIGS. 9a, b). The enhanced response of the frozen-thawed cells was susceptible to SOD inhibition, indicating that the increased lucigenin-dependent chemiluminescence involved an increase in superoxide anion production. Alterative methods for permeabilizing the spermatozoa, including the use of Triton X were also compatible with the induction of chemiluminescent responses to NAD(P)H (data not shown). In contrast, sperm suspensions that were immobilized by incubation at 57° C. for 30 min did not generate superoxide anion in response to exogenous NADPH, nor did those cells fixed with 0.25% glutaraldehyde prior to NADPH addition (FIG. 9b). Glutaraldehyde also inhibited the NADPH response in cells that had previously been permeabilized by freeze thawing (FIG. 9a). These results suggested that NADPH had to interact with the inner leaf of a functional sperm plasma membrane and/or a cytoplasmic constituent in order to generate ROS. The importance of the plasma membrane as a site of superoxide generation was indicated by experiments in which chemiluminescent responses were generated by exposing purified sperm plasma membranes to NADPH (data not shown).

Pharmacology of ROS Response

Figure 12A:
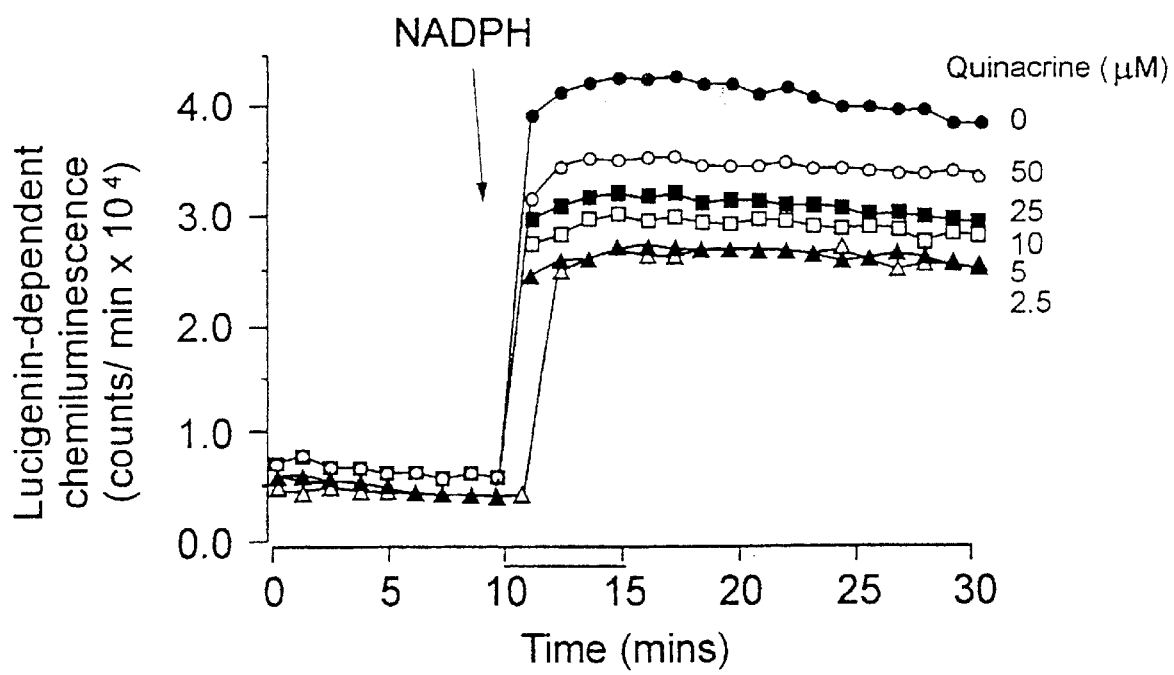
Figure 12B:
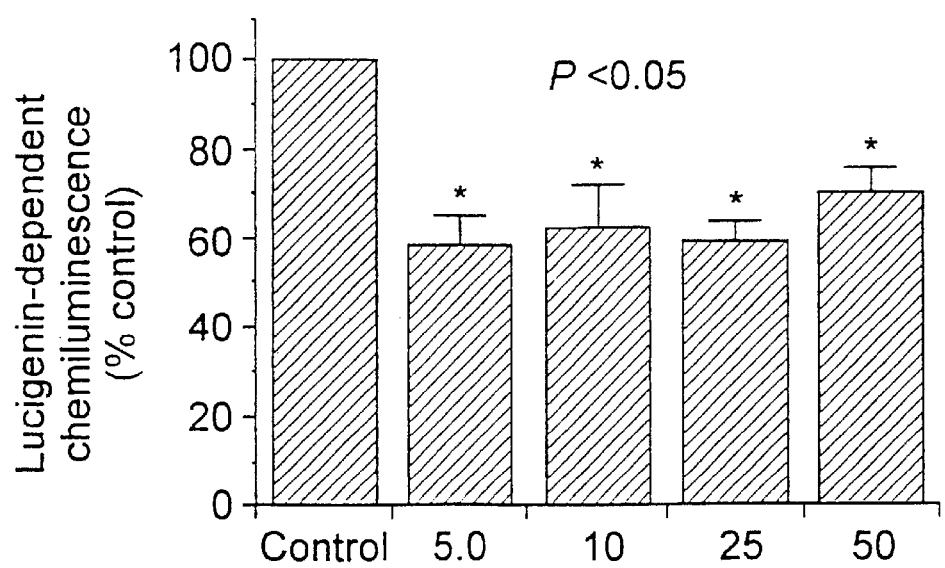
Figure 12C:
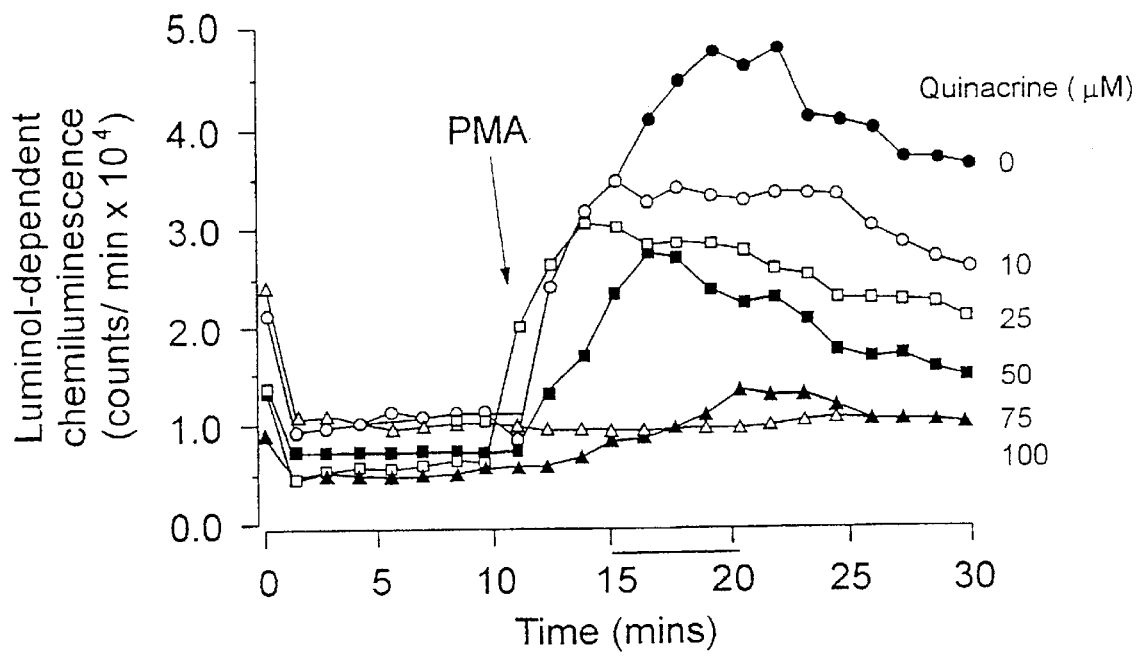
Figure 12D:
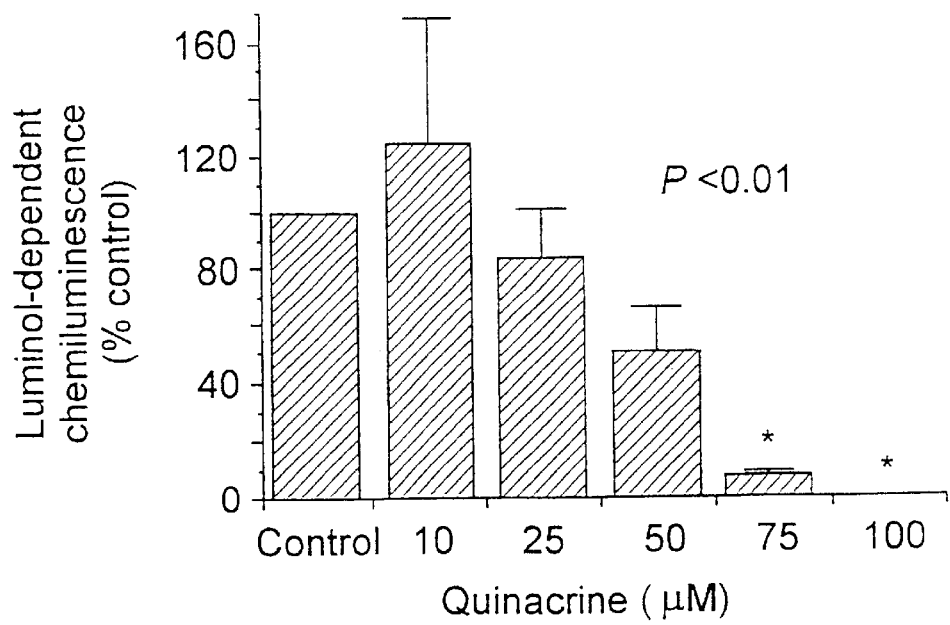

DPI exhibited a dose-dependent capacity to suppress NADPH-induced free radical generation, that was statistically significant at the 1 μM level (P<0.001; FIGS. 10a, b). DPI was also competent to inhibit the stimulation of hydrogen peroxide production by PMA over a dose range extending from 0.01–100 μM (FIGS. 11a, b, P<0.001). The possibility that a flavoprotein is involved in mediating ROS generation by human spermatozoa was also supported by the ability of quinacrine to suppress the responses to PMA in a dose-dependent manner, with a complete loss of activity observed at doses of 75–100 M (P<0.001; FIGS. 12c, d). Quinacrine also inhibited the capacity of NADPH to induce superoxide generation by human spermatozoa (P <0.001; FIGS. 12a, b) although in this case, a dose/response relationship was not observed and quinacrine concentrations as high as 50 μM could only suppressed NADPH-induced ROS production by 30–40%.

The possible involvement of the sperm mitochondria in the responses of human spermatozoa to NADPH was examined using a range of inhibitors of the mitochondrial electron transport chain including antimycin A, rotenone, carbonyl cyanide m-chlorophenylhydrazone (CCCP) and sodium azide, none of which were effective (Table 1).

TABLE 1

Influence of mitochondrial inhibitors on
NADPH-induced ROS generation by human spermatozoa.

| Inhibitor | Treatment | Lucigenin dependent chemiluminescence (counts/5 min × 10⁴)* |
|---|---|---|
| Antimycin A (50 µM) | Control | 10.17 ± 2.16 |
|  | Treated | 10.53 ± 2.49 |
| Rotenone (10 µM) | Control | 9.62 ± 1.68 |
|  | Treated | 9.07 ± 2.26 |
| CCP (10 µM) | Control | 14.99 ± 8.77 |
|  | Treated | 12.61 ± 6.97 |
| Sodium azide (10 µM) | Control | 8.62 ± 0.98 |
|  | Treated | 7.69 ± 1.54 |

*Data presented as means ± SE

To rule out the possibility that these reagents were not gaining access to the mitochondrial membranes, a range of inhibitors (oligomycin, antimycin A and rotenone) were also examined in triton permeabilized cells and again no inhibition of the response to NAD(P)H was observed. Inhibitors of other potential mechanisms for NADPH-dependent reactive oxygen species generation. were also assessed and found to be ineffective, including dicoumarol (100 µM) an inhibitor of DT-diaphorase, sodium oxamate (1 mM) an inhibitor of lactate dehydrogenase and allopurinol (10 mM) an inhibitor of xanthine oxidase (Table 2). Thus the ability of human spermatozoa to generate ROS did not appear to be a by-product of cell metabolism, but a. specialized activity utilizing NAD(P)H as substrate and featuring the possible participation of a flavoprotein in the electron transport chain.

TABLE 2

Influence of various inhibitors on NADPH-
induced superoxide generation by human spermatozoa.

| Inhibitor | Treatment | Lucigenin dependent chemiluminescence (counts/5 min × 10⁴)* |
|---|---|---|
| Sodium Oxamate (1 mM) | Control | 4.88 ± 2.04 |
|  | Treated | 5.20 ± 2.10 |
| Dicoumarol (100 µM) | Control | 4.30 ± 1.71 |
|  | Treated | 5.20 ± 2.10 |
| Allopurinol (10 mM) | Control | 7.54 ± 2.06 |
|  | Treated | 7.19 ± 1.66 |

*Data presented as means ± SE

DISCUSSION

A number of compounds have been demonstrated to have spermicidal activity with 1,4-naphthoquinone and juglone being preferred examples. Such compounds can produce a dose-dependent inhibition of human sperm motility. On contact with sperm these compounds may produce a rapid but transient rise in ROS overwhelming the inherent but limited antioxidant capacity of sperm. Resultant peroxidative damage to the sperm plasma membrane can alter membrane fluidity thereby compromising sperm motility and sperm-oocyte fusion. The rapidity of this increase in ROS production in human sperm response also indicates that this is the preferred mechanism responsible for the spermicidal actions of these quinones. Not all quinones are cytotoxic and indeed the aforementioned inhibition of sperm motility as well as ROS generation in human sperm is also quinone-dependent.

The virucidal activity of 1,4-naphthoquinone and juglone were significantly enhanced in the presence of human semen.

The primary product of the free radical generating system in sperm may be the $O_2^-$ which secondarily dismutates to $H_2O_2$ under the influence of intracellular superoxide dismutase. However, the detailed biochemical mechanism by which ROS are generated by mammalian spermatozoa have yet to be elucidated for any species.

In purified populations of spermatozoa, ROS is correlated with glucose-6-phosphate dehydrogenase activity. We have confirmed that human spermatozoa are able to utilise NADPH as a substrate for ROS generation. Moreover, this activity could be induced in suspensions of viable, motile spermatozoa by the addition of NADPH to the ambient medium. It is possible that NADPH exerts its effects by penetrating through the sperm plasma membrane and interacting with one or more intracellular oxidase-like enzymes located in the cytoplasm and/or the cytoplasmic surface of the plasma membrane.

An additional corollary of this hypothesis is that the heterogeneity observed between individuals in the responsiveness of their spermatozoa to NADPH might reflect differences in the permeability of the plasma membrane as a consequence of variations in lipid composition or peroxidative damage (Jones and Mann, 1973; Alvarez and Storey, 1982).

The inactive, unassembled NADPH oxidase of phagocytic leukocytes does not generate ROS in response to exogenous NADPH, although the active assembled oxidase does. Such findings suggest that the spermatozoons free radical generating system differs from the NADPH oxidase of phagocytes in requiring no prior activation; instead, substrate availability is a key controlling factor. In addition to acting as a substrate for the spermatozoons free radical generating system, NADPH may also serve as a co-factor for the conformational modification of the putative oxidase system to an activated superoxide-generating state Modifications and improvements may be incorporated without departing from the scope of the invention.

REFERENCES

Aitken R J, Buckingham D W, Harkiss D, Paterson M, Fisher H, Irvine D S (1996): Molec Cell Endocrinol 117:83–93.
Aitken R J, Buckingham D W, West K M (1992): J Cell Physiol 151: 466–477.
Aitken R J, Clarkson J S (1987): J Reprod Fert 81:459–469.
Aitken R J, Clarkson J S (1988): J Androl 9: 367–376.
Aitken R J, Hulme M J, Henderson C J, Hargreave T B, Ross A (1987): Fert 80: 473485.
Aitken R J, Krausz C, Buckingham D W (1994): Molec Reprod Dev 39:Z68–279.
Aitken R J, Paterson M, Fisher H, Buckmgham D W, van Duin M (1995): J Cell Science 108:2017–2025.
Alvarez J G, Storey B T (1982): Biol Reprod 27:1102–1108.
Alvarez J G, Storey B T (1984): Biol Reprod 30:833–841.
Alvarez J G, Touchstone J C, Blasco L, Storey B T. (1987): J Androl 8:338–348.
Bellavite P (1988): Free Rad Biol Med 4:z25–261.
Biggers J D, Whitten W K, Whittingham D G (1971): In J C Daniel (ed): "Methods in Mammalian Embryology." San Francisco: Freeman, pp 86–94.
Cross A R (1990): Free Rad Biol Med 8:7193.
Cross A R, Jones O T G (1986): Biochem J 237:111–116.
Cross A R, Jones O T G.(I991): Biochem Biophys Acta 1057:281–298.
De Lamirande E, Gagnon G (1993): Free Rad Biol Med 14:157–166.

Deme D, Dousierre J, De Sandro V, Dupuy C, Pommiere J, Virion A (1994): Biochem J 301:75–81.
Dousierre J, Vignais v (1991): Biochem Biophys Res Comm 175:143–151.
Dousietre J, Vignais V (1992): Eur J Biochem 208:61–71.
Ellis J A, Mayer S, Jones OTG (1988): Biochem J 251:887–891.
Ferrante A, Rowan Kelly B, Seow W K, Thong Y H (1986): Immunology 58:125–130.
Fujii H, Kakinuma K (1991): Biophys Acta 1095:201–209.
Goldman R, Ferber E, Zort U (1992): FEBS Lett 309:190–192.
Hancock J T, Jones OTG (1987): Biochem J 242:103–107.
Holland M K, Alvarez J G, Storey B T (1982): Biol Reprod 27:1109–1118.
Iawasaki A, Gagnon C (1992): Fertil Steril 57:409–416.
Jones R, Mann T (1973): Proc R Soc Lond B Biol Sci 184:103–107.
Krausz C, West K, Buckingham D, Aitken J (1992): Fertil Steril 57: 1317–1325.
Kreiger-Brauer Hl, Kather H (1992): J Clin Invest 89:1006–1013.
Lasso J L, Noiles E E, Alvarez J G, Storey B T (1994): J Androl 15: 255–265.
Lessley B A, Garner D L (1983): Gamete Res 7:49–61.
MacLeod J (1943): Am J Physiol 138: 512–518.
Maly F E, Cross A R, Jones O T G, Wolf-Vorbeck G, Walker C,
Dahinden C A, De Weck. (1988):J Immunol 140:2334–2339.
McCord J M, Fridovich I (1969): J Biol Chem 244:6049–6055.
Meier B, Cross A R, Hancock J T, Kaup F J, Jones O T G (1991): Biochem J 275:241–245.
Meier B, Jesaibs Al, Emmendorffer A, Roesler J, Quinn M T. (1993): Biochem J 289:481486.
Meier B, Radeke HH, Selle S, Younes M, Sies H, Reseh K, Habermehl GG. (1989): Biochem J 263:539–545.
Ngugi et al Barrier Contraceptives, 261–264, Willey Liss, 1994

O'Donnell VB, Tew D G, Jones O T G, England P (1993): Biochem J 290: 41–49.
Radeke H H, Cross A R, Hancock J T, Jones O T G, Nakamura M, Kaever V, Resch K (1991): J. Biol Chem 266: 21025–21029.
Schieven G L, Kirihara J M, Burg D L, Geahlen R L,
Ledbetter J A (1993): J Biol Chem 268:16688–16692.
Silverton S F, Mesaros S, Markham G D, Malinski T (1995) Endocrmology 136:52445247.
Sharpe et al Environ. Health Prospect. 103, 1136–1143, 1995
Smith R M, Curnutte J T, Babior B M. (1989): J Biol Chem 264:1958–1962.
Staal F J T, Anderson M T, Staal G E J, Herzenberg L A, Gitler C and Herzenberg L A (1994): Proc Natl Acad Sci USA 91:3619–3622
Sundquist T (1991): J Cell Physiol 148:152–156.
Tan C M, Xenoyannis S, Feldman R D (1995): Circ Res 77:710–717.
Tosic J, Walton A (1946): Nature 158: 485.
Tosic J and Walton, A. (1950): Biochem J 47:199–212.
World Health Organization (1992) "WHO semen manual for the examination of human semen and cervical mucus interaction". Cambridge UK: Cambridge University Press.

What is claimed is:

1. A method of contraception comprising exposing a spermicidally sufficient quantity of an agent to ejaculated spermatozoa, the agent being 1,4-naphthoquinone or juglone, wherein said agent undergoes a one electron reduction to the corresponding semiquinone when in the presence of spermatozoa, and wherein upon contact with spermatozoa the agent generates reactive oxygen species including free radicals, superoxide and hydrogen peroxide thereby causing spermatozoa exposed thereto to be immobilised such that the spermatozoa has a mean motility score of or less.

2. A method of contraception as claimed in claim 1 wherein the agent is 1,4 naphthoquinone.

* * * * *